United States Patent [19]

Keller

[11] Patent Number: 5,210,025
[45] Date of Patent: May 11, 1993

[54] REPRESSOR PROTEIN GENE FOR REGULATING EXPRESSION OF POLYPEPTIDES AND ITS USE IN THE PREPARATION OF 2,2-DIALKYLGLYCINE DECARBOXYLASE OF PSEUDOMONAS CEPACIA

[75] Inventor: John W. Keller, Fairbanks, Ak.

[73] Assignee: University of Alaska, Fairbanks, Ak.

[21] Appl. No.: 501,814

[22] Filed: Mar. 30, 1990

[51] Int. Cl.[5] .................. C12N 15/00; C12N 15/54; C12N 15/70
[52] U.S. Cl. .................. 435/69.1; 435/143; 435/252.33; 435/320.1; 536/23.2
[58] Field of Search ............... 435/69.1-69.4, 435/172.1-172.3, 320.1, 252.3-252.35, 252.33; 536/27

[56] References Cited

PUBLICATIONS

Sato, S. et al., 1978, Agricultural and Biological Chemistry (Tokyo), 42: 2341-2346.
Aaslestad, H. G. and A. P. Larson, 1964, Journal of Bacteriology, 88: 1296-1303.
Keller, J. W. et al., 1988, FASEB Journal 2(5): Abstract 6111 (Abstract for FASEB Annual Meeting, May 1-5, 1988).
Keller, J. W. et al., 1989, Journal of Cell Biology 107 (6 punt 3): (Abstract 2276) 399A (Abstract for Joint Meeting Am. Soc. Cell Biol. and Am. Soc. Biochem Med. Biol. 1989).
Keller et al., Pseudomonas cepacia 2,2-Dialkylglycine Decarboxylase-Sequence and Expression in Escherichia Coli of Structural and Repressor Genes, J. Biol. Chem. 265(10):5531-5539 (1990).

Primary Examiner—Robert A. Wax
Assistant Examiner—William W. Moore
Attorney, Agent, or Firm—Finnegan, Henderson, Farabow, Garrett & Dunner

[57] ABSTRACT

A nucleotide sequence coding for a repressor protein for regulating gene expression comprises about a 687 bp nucleotide region beginning about 81 bases upstream from the 2,2-dialkylglycine decarboxylase structural gene shown in FIG. 3. The repressor protein comprises about 229 amino acids. The nucleotide sequence is useful for regulating gene expression in recombinant expression vectors. The vectors and E. coli cells transformed with the vectors are useful for preparing Pseudomonas cepacia 2,2-dialkylglycine decarboxylase.

3 Claims, 11 Drawing Sheets

FIG. 3A

```
1331 TCCATCAAAACAGACGCGGCGGCCTAGACTGCGAAGGCGATCCCTGCCCCCTTGCCCGGAAGCCCGATGTCC                                   2
                                                                            MetSer>

1401 CTGAACGACGATGCAACCTTCGGGCGCAGACCTGTCCGCAACGCAGGCAGACACCTGTCCGCTACGGGCGGCACGTTCGAGC                        25
     LeuAsnAspAspAlaThrPheArgArgAsnAlaArgGlnHisLeuValArgThrGlyValThrPheGlu>

1471 CGATGATCATCGAGCGCGGCGAAGGGCAGCTTCGTCTATGACGCCGACGGCGCCGCGGATCCTCGATTTCAC                                  49
     ProMetIleIleGluArgGlyGluGlyGlnLeuArgLeuTyrAspAlaAspGlyAlaIleLeuAspPheThr

1541 GTCGGGCGAGATGAGCGGCGGGTCTCGGCCACTGCCATCCTGCCACTCGGAGATCGTCTCCGTCATCGGGAATACGCG                            72
     SerGlyGluMetSerGlyGlySerProLeuProSerHisCysHisProGluIleValSerValIleGlyGluTyrAla>

1611 GGCAAGCTCGATCACCTGTTCAGCGAATCGTGTTCAGCGGGAATCGTGTCGACCTCGACGCGCCTCGCCA                                    95
     GlyLysLeuAspHisLeuPheSerGlyIleValSerArgProValValAspLeuAlaThrArgLeuAla>

1681 ACATCACGCCGCCCGGGCTCGACCCGGCTCGTGTCTCAGCGGCCGGGAATCGAACGAAGGCAATCG                                       119
     AsnIleThrProProGlyLeuAspArgAlaLeuLeuLeuSerThrGlyAlaGlySerAsnGluAlaAlaIle>

1751 CCGGATGGCGAAGCTCACCGGCAAGTCGTCGGCTTCGGCGTTCGCCAGTCGTGGCAGTCGTGGCACGGGATGACG                              142
     ArgMetAlaLysValThrGlyLysTyrGlyIleValGlyPheAlaGlyPheAlaGlnSerTrpHisGlyMetThr>

1821 GGGCGGCCGCATCGGCCACGGCTACAGCGCGGGCCCGTGTCGGCCCGAAGGGTGTCGGCGTGAGGCGGCTCGTTCG                             165
     GlyAlaAlaSerAlaThrTyrSerAlaGlyArgGlyLysGlyValGlyProAlaAlaValGlySerPhe>

1891 CGATTCCGGCGCCATTCACGTACCGGCCGCCTTCGAGCGCAACGGCGTACGACTATCTCGCCGAACT                                      189
     AlaIleProAlaProPheThrTyrArgProArgPheTyrArgProArgGluArgAsnGlyAlaTyrAspTyrLeuAlaGluLeu>

1961 CGACTACGCGTTCGACCTGATGACGAACCTGAACTGCAGAGTGGCAACCTCGGGCAACCTCGGGAGCCGATC                                 212
     AspTyrAlaPheAspLeuIleAspArgGlnSerSerGlyAsnLeuAlaAlaPheIleAlaGluProIle>

2031 CTCAGTTCGGGGCGGGATCATCGAACTGCCGACGCGCTACATGCCGGACGGCTACAAGGCGACGGCAAGGCGC                                235
     LeuSerSerGlyGlyIleIleGluLeuProAspGlyTyrMetAlaAlaLeuLysLysArgLysCysGluAla>

2101 GCGGGATGCTGCTGATCCTCGACGAGGCAGAGGGCGTCGACGACCACCGGACGATGTTCGCGTGCCA                                      259
     ArgGlyMetLeuLeuIleLeuAspGluAlaGlnThrGlyValGlyArgThrGlyValGlyArgThrGlyMetPheAlaCysGln>

2171 GCGCGACGGCGTGACGCCCGACATCCTGACCGTGTCGAAAACGCTCGGCGCCTGCGCCTCGCGGCC                                       282
     ArgAspGlyValThrProAspIleLeuThrLeuSerLysThrLeuGlyAlaGlyLeuProLeuAlaAla>

2241 ATCGTGACGTCCGGGCGATCGGAGAACGGCGACGAACTCGGCTACCTGTTCTATACGACGCACGTGT                                      305
     IleValThrSerAlaAlaIleGluGluArgAlaHisGluGluThrGlyLeuTyrLeuPheTyrThrThrHisVal>
```

```
2311 CCGATCGCTGCCCCCGGGCCGGGCTCGGCCTGCGCGTCGGCGTCGGTGCTGCAGGCGGGCGACGGGCTCGTCGC    329
     SerAspArgCysProProAlaGlyValGlyLeuArgValGlyLeuAspValValGlnArgAspGlyLeuValAla>

2381 ACGGCGAACGTGATGGGCGACCGGCTCAGGGCGCGGCCTGCTCGACCTGATGGAGCGGTTCGACTGCATC        362
     ArgAlaAsnValMetGlyAspArgLeuArgArgGlyLeuArgLeuAspLeuMetGluArgPheAspCysIle>

2451 GGGCGACGTGCGCGGGCGCGGGGCGCTGCTCGGCGTCGAGATCGTCAAGGATCGTGACGCACGAAAGAGCCGG    375
     GlyAspValArgGlyArgGlyArgGlyLeuLeuGlyValGluIleValLysAspArgArgThrLysGluPro>

2521 CGGACGGCCTCGGCGGCGAAGATCACGCGCGAGTGCATGAACCTCGGGCTCAGCATGAACATCGTGCAGTT      399
     AlaAspGlyLeuGlyAlaLysIleThrArgGluCysMetAsnLeuGlySerMetAsnIleValGlnLeu>

2591 GCCCGGCATGGGCGGCGGCGTGTTCCGGATCGCCGCCGCTGACGGTCAGCGAGGACGAGATCGATCTGGC      422
     ProGlyMetGlyGlyValPheArgIleAlaProProLeuThrValSerGluAspGluIleAspLeuGly>

2661 TTGTCGCTGCTCGGTCAGGCGATCGAACGCGCGCTGTAACGCCCGCCGGTAACGCCCTTCTCCGCAT          434
     LeuSerLeuLeuGlyGlnAlaIleGluArgAlaLeuEnd>

2731 CGTGCGATTCGTCGCGCCCGGTTCGAGCGCCGACGGATTCCCGATCGATCAGCGCGTTTCGGCCG
2801 CCCACGCTTCGGCGGCATCGGCGGCGGAATGCGCATCGGGCTCGACGGGCTCCGCTCCGCGGCCACAC
2871 GGCGTCGGCAACATCCTGCGCACGGGTGATCGGCCCGGGTGTTCGAAGCGAGCATCGAGACTCCTCCG
2941 GCGAACTCCGCACGGCCATAAGCCTCGTGTCGCAGCACGGCCATGCGCGAACGGTTCGAGTTCGAACGCGTGT
3011 CCGGGTGCAACGCCCGGCAGCAGCCGCCTTGACGCCCGATGTGCTGGCCGGCAATGCGGGCAACACCTTCAGCGTGAC
3081 CGGTGAACGGCATTGACGTTGCAGTCGTGCGGACGACACGCGCACGGTTCGACGGCAACTGCGGGGAGCTCGGCTGC
3151 GCTCGACGTCGTGCGCGAAGCCTTCGTCGCGACGGGTTCGGAGACCCAGCAGTGATCGCTGCGGATGGCACGTCGGGA
3221 CGCAATCGTGCCGCGCGCCGGCGAAGCGTTCGTCGCGGGTGACCGGAACCAGGCCCAGGGAACTCGGGGCTCCTCGCG
3291 GGGCGCGCCGGGGGCGCCGGGTCCGCGCGGTCGTCGTGGGCCGATCGGGATGGCACGTCGGGCAATCTCGAGGCCGAAGC
3361 TGCTGTGCGACAGCCCGGCGGGAACAGCGGCCAGTGCTCTTCATGCGAAATGCAAACCAGGCGCGAAAGCGCGAAGC
3431 CGGTGTGAAGGAACCGCGGTCGGATCGAACCTACGGCTCTACAATGGCGAAGCTGGCATGTCGGCATGTCCGGATGAT
3501 GATAGATAGCGGGCCAGTGATCAGTATTCGCTGAGCCGTTCTCTGCTGCTTATTGGCGAAAGCAAATGCTCAAAGCGCG
3571 CGACCCGTTGATCAACAGCTGCTGGGTCCCGGGTCGACAGCGGGTACTCCAAAGCGCGGAACCCGGCGCTCAGGGCGCG
3641 ACGCGTGGTCCGCGAACGCCGCTGGTCGATTCGTGCGACTTCGTCGTCTGCGCATTCGTGCGCAAAGCGCGGATCCTGGCG
3711 CACGGCGATCAACGCGGCGAAACAGGGGTCGAAATCAGGCGATCCTGCTGATTTCGTGCGAAAGCGGGTCAACGTCCA
3781 GCCTCGAACCGGCAACGCGCCGCCGGCGTGCACTCGCACTCGACAACGGCGGCCACTCGACAACGGGCGAATACCGGAT
3851 CGGCGATCGGGCAACCCCGTCGACACGGCGGGCAACTGCAG
```

FIG. 3B

```
1410 AGGTTGCATCGTCGTTCAGGGACATCGGGCTTCTCCGGGCAAGGGGGCAGGGATCGCTTG

1350 CAGTCTAGGCGCGCGTCTGTTTTGATGGAAACGAATAGTTCTTATGCAAGGTAGAAAGGG
                                              M  Q  G  R  K  G   5

1290 GGCTAATACCTTGGGACGCTCGCTCGAAATCGACCTGCTGCGTTCGTTCGTCGTGATCGC
      A  N  T  L  G  R  S  L  E  I  D  L  L  R  S  F  V  V  I  A   25

1230 CGAGGTGCGCGCGCTCAGCGCGGCCGCGCGCGTCGGCCGGACGCAGTCCGCGCTCAGCCA
      E  V  R  A  L  S  A  A  A  R  V  G  R  T  Q  S  A  L  S  Q   45

1170 GCAGATGAAGCGGCTCGAGGATATCGTCGACCAGCCGCTGTTCCAGCGCACCGGCCGCGG
      Q  M  K  R  L  E  D  I  V  D  Q  P  L  F  Q  R  T  G  R  G   65

1110 CGTGGTGCTGACGCACCCCGGCGAGCGGCTGCTCGTGCATGCGCAGCGCATCCTGCGGCA
      V  V  L  T  H  P  G  E  R  L  L  V  H  A  Q  R  I  L  R  Q   85

1050 GCACGACGAGGCAATGGCCGACCTGTGCGGCACGGGGTTGACGGGGACGATCCGGTTCGG
      H  D  E  A  M  A  D  L  C  G  T  G  L  T  G  T  I  R  F  G  105

990 GTGCCCGGACGATTACGCGGAGGTGTTTCTGCCGCCGCTGCTGCGGCAGTTTTCGAGCCA
      C  P  D  D  Y  A  E  V  F  L  P  P  L  L  R  Q  F  S  S  Q  125

930 GCATCCGCAGGCGATCGTCGAAATCGTATGCGGGCCGACGCCGCGGCTGCTCGAACAGCT
      H  P  Q  A  I  V  E  I  V  C  G  P  T  P  R  L  L  E  Q  L  145

870 CGAGAAGCGCGCGGTCGATCTCGCGATGATTTCATTGCCGGACGATGGGGCGAACGACGA
      E  K  R  A  V  D  L  A  M  I  S  L  P  D  D  G  A  N  D  D  165

810 CATCATTCGTCGCGAGCAGCTGGTCTGGATCGGCTATCCGGGGCTGGAGCCCGCGCATTT
      I  I  R  R  E  Q  L  V  W  I  G  Y  P  G  L  E  P  A  H  F  185

750 CGATCCGCTGCCGCTCGCGCTGTCCGATCCCGATACGCTCGATCACATCGCGGCCTGCGA
      D  P  L  P  L  A  L  S  D  P  D  T  L  D  H  I  A  A  C  D  205

690 CGCGTTGCATCGCGCCGGTCGCGATTACCGCGTCGCGTATGCGAGCAGCAGTCTCGCGGG
      A  L  H  R  A  G  R  D  Y  R  V  A  Y  A  S  S  S  L  A  G  225

630 GCTGATCGCGCTGGTGCGCTCGGGGCAGGCGTTCGCGGTGATGACGCAGACGGCCGTGCC
      L  I  A  L  V  R  S  G  Q  A  F  A  V  M  T  Q  T  A  V  P  245

570 GGCCGACCTGGCGATCGTCAACGGCGATCCGCGGTTGCCGCCGTTGCCGGCGGTGGGCAT
      A  D  L  A  I  V  N  G  D  P  R  L  P  P  L  P  A  V  G  I  265

510 TACGCTGAAGTTCGACCGGAAACGGCCGTCGCATCTGACGGCGGCGTTCGCCGAGCATAT
      T  L  K  F  D  R  K  R  P  S  H  L  T  A  A  F  A  E  H  I  285

450 TCGGGCCGTGTTGCCGATGCTGTGACGCGAAGTCGTCGCGCCGGAAACGCAGGCATCGAC
      R  A  V  L  P  M  L                                          292

390 GCGGGATTCGAGGCGTCGACGTTTGCCGTCCATCTGACCGAGTGCTTCGTTCCGCATCGC
 330 CGAAGCAATAAAAAAACCCGCGAAGCCATGCGCTGTCGCGGGTTTTGCAAATGCACGAAA
 270 CACGGAAAAACCGTATTTGGTGCCGACGGCGAGACTCGAACTCGCACAGCTTTCGCCACT
 210 ACCCCCTCAAGATAGCGTGTCTACCAATTTCACCACGTCGGCACTGCAAGGGGCCGAATT
 150 GTAGCGTTACCATCGCGCGTTTGTGAAGAGGGTGTGACACGGCGAGCGGATGCGTGAAAG
  90 CGATCCCGGTAGAATTCGGACGATCGGTCCGACGACCATCGCTACTGCCATCCGCTTTCT
  30 CCCCGTGACCACCACCCTCGAACAACTGCAG*
```

| | | | | | |
|---|---|---|---|---|---|
| P. cepacia DGD[1]        | V T P D I L T - - - | L S K T L G A G L - - - | P L A A - - | I V T |
| Mammalian OrnAT[2]       | V R P D I V L - - - | L G K A L S G G L Y - - | P V S A - - | V L C |
| Yeast OrnAT[3]           | A K P D I V L - - - | L G K A L S G G V L - - | P V S C - - | V L S |
| Chick. Mito. AspAT[4]    | P G I D V V L S Q S | Y A K N M - - G L Y G E R | A G A F - | V - C |
| Pig Cyto. AspAT[5]       | E G F E L F C A Q S | F S K N F - - G L Y N E R | V G N L T | V V A |
| Pig Cyto. AspAT[6]       | M H K E L I V A S S | Y S K N F - - G L Y N E R | V G A C T | L V A |
| E. coli AspAT            | Q G I D I L - Y S G | S Q K V L V A P P G I S L | I S F N D K A K | |
| Rat Mito. SerAT[7]       | | | | |
| Pig Heart AlaAT[8]       | Q E L A S F H S V S | K G F M G E C - G F R | | |

REPRESSOR PROTEIN GENE FOR REGULATING EXPRESSION OF POLYPEPTIDES AND ITS USE IN THE PREPARATION OF 2,2-DIALKYLGLYCINE DECARBOXYLASE OF PSEUDOMONAS CEPACIA

BACKGROUND OF THE INVENTION

This invention relates to a purified nucleotide sequence coding for a repressor protein for regulating gene expression. In addition, this invention relates to a recombinant expression vector containing the nucleotide sequence, an *E. coli* cell transformed or transfected with the recombinant expression vector, and the use of the *E. coli* cells for preparing *Pseudomonas cepacia* 2,2-dialkylglycine decarboxylase. Further, this invention provides a repressor protein encoded by the nucleotide sequence, wherein the repressor protein is in a purified form.

The 2,2-dialkylglycine decarboxylase of the soil bacterium *Pseudomonas cepacia* was first reported by Aaslestad and Larson (1964) and was later investigated in several laboratories (Bailey and Dempsey, 1967; Bailey et al., 1970; Lamartiniere et al., 1971; Honma et al., 1972; Sato et al., 1978; and Keller and O'Leary, 1979). This pyridoxal 5'-phosphate-dependent enzyme catalyzes decomposition of substrate amino acids such as 2-methylalanine and isovaline in two steps: (i) release of carbon dioxide and ketone with transfer of the amino group to the cofactor to give enzyme-bound pyridoxamine 5'-phosphate and (ii) amino transfer from cofactor to pyruvate forming L-alanine and regenerating the cofactor in the aldehyde oxidation state. The decarboxylation step is analogous to the so-called abortive decarboxylation catalyzed by several pyridoxal 5'-phosphate-dependent amino acid decarboxylases, which competes with the normal hydrogen for carboxylate replacement reaction (Sukhareva, 1986). The dialkylglycine decarboxylase is of interest because it normally catalyzes both decarboxylation and amino transfer. Therefore, the question arises whether this enzyme is an aminotransferase that through evolution has added a decarboxylase capability or is a decarboxylase that has evolved an amino transfer capability. A preliminary answer as provided to this question by showing that the dialkylglycine decarboxylase primary structure is homologous to several aminotransferases but not to decarboxylases.

The biological role of the dialkylglycine decarboxylase remains unclear. The substrates 2-methylalanine and isovaline occur naturally as major constituents of cytotoxic peptides produced by soil fungi such as *Trichoderma viride* (Bruckner et al., 1980; Bruckner and Pryzbylaki, 1984; Schmitt and Jung, 1985) and as organic components of carbonaceous meteorites (Kvenvolden et al., 1971). Racemic isovaline and 2-methylalanine have been found recently in an iridium-rich Cretaceous-Tertiary boundary layer, further supporting an extraterrestrial source for this material (Zhao and Bada, 1989). Thus, the enzyme may have evolved to use the rare dialkylglycines of cosmic origin, or it may be a part of a metabolic pathway for breaking down cytotoxic peptides and the constituent amino acids.

The available structural information about the 2,2-dialkylglycine decarboxylase is sparse. Lamartiniere et al. (1971) showed by equilibrium sedimentation that a dialkylglycine decarboxylase isolated from P. cepacia has a molecular mass of 188 kDa with four identical 47-kDa subunits. They also reported a peptide map and amino acid composition data consistent with a 47-kDa subunit. Sato et al, (1978) also studied the *P. cepacia* dialkylglycine decarboxylase, showing by gel electrophoresis that the 180-kDa holoenzyme contained four identical subunits of approximately 45 kDa and presenting chemical labeling evidence for a catalytically important histidine residue.

SUMMARY OF THE INVENTION

Aaslestad and Larson (1964) found that the *P. cepacia* produced the decarboxylase only when the organism's minimal salts-glucose growth medium was supplemented with 2-methylalanine. This suggested that decarboxylase gene expression is induced in some way by the dialkylglycine substrate. This question was reexamined using the cloned and sequenced *P. cepacia* DNA. We report here that the cloned DNA codes for an intact dialkylglycine decarboxylase repression-induction system that functions in *Escherichia coli*. Functional analysis of partially deleted plasmids and computer analysis of the sequence upstream of the structural gene provide evidence for a repressor gene. Also, several 2,2-dialkylglycine stereoisomers were synthesized and tested as inducers of decarboxylase gene expression.

More particularly, this invention provides a purified nucleotide sequence coding for a repressor protein for regulating gene expression. The nucleotide sequence comprises about a 687 bp nucleotide region beginning about 81 bases upstream from the 2,2-dialkylglycine decarboxylase gene which is shown in FIG. 3. The gene codes for the repressor protein, which comprises about 229 amino acids.

This invention also provides recombinant expression vectors pKBD6, pUC19C7, pGEM-7Z14 which contain the nucleotide sequence coding for the repressor protein, as well as the recombinant expression vector pGEM-7Z14/3e.

In addition, this invention provides an *E. coli* cell transformed with the recombinant expression vectors of the invention.

Also, this invention provides a process for preparing *Pseudomonas cepacia* 2,2-dialkylglycine decarboxylase. The process comprises providing a biomass comprised of *E. coli* cells of the invention. The *E. coli* cells are cultured in the presence of a gene inducing agent selected from the group consisting of S-isovaline, 2-methylalamine, L-2-aminobutanoic acid, or 1-aminocyclopentane carboxylic acid. The gene inducing agent is employed in the biomass in an amount sufficient to induce transcription of the *Pseudomonas capacia* 2,2-dialkylglycine decarboxylase gene in the cells. The process of this invention makes it possible to express the decarboxylase gene at higher levels than in *Pseudomonas cepacia*.

When *E. coli* cells of the invention transformed with pUC19C7, pGEM-7Z14, or pGEM-7Z14/3e are used in a process for preparing *Pseudomonas cepacia* 2,2-dialkylglycine decarboxylase, they may also be cultured in the presence of isoproply-1-thio-b-D-galactopyranoside (IPTG) to induce a lac operon and carbenicillin, a penicillin analog, to force *E. coli* cells to maintain the plasmids inside each cell. These plasmids carry a gene for penicillinase, an enzyme that deactivates the carbenicillin antibiotic.

Finally, this invention provides a purified repressor protein comprised of the amino acid sequence of the repressor protein shown in FIG. 4.

BRIEF DESCRIPTION OF THE DRAWINGS

This invention will be more fully described with reference to the drawings in which:

FIGS. 3A and 3B shows the nucleotide sequence of the cloned P. cepacia DNA (3′ of the + strand) with the deduced amino acid sequence of the 2,2-dialkylglycine decarboxylase structural gene. Underlined amino acid residues were verified by automated sequencing of the purified recombinant dialkylglycine decarboxylase and the active site peptide; low yield or uninterpretable cycles are denoted by dotted lines. A ribosome binding site is underlined, and a possible transcription termination site is overlined.

FIG. 4 shows the nucleotide sequence of the cloned P. cepacia DNA (3′ end of the − strand) with the predicted amino acid sequence of the repressor protein. The numbering of the + strand is retained. Underlined is a possible ribosome binding site. Overlined are the nucleotides complementary to the first 16 nucleotides of the dialkylglycine decarboxylase structural gene.

FIG. 9 is an alignment of deduced sequences of 2,2-bialkylglycine decarboxylase (this work) and rat ornithine aminotransferase (Mueckler and Pitot, 1985). A modification of the method of Needleman and Wunsch (1970) with a window of 30, a gap penalty of 10, and a size penalty of 2 was used. Identical residues or conservative substitutions are boxed. Active site lysines are marked by dots.

FIG. 10 is an alignment of active site peptides of several pyridoxal 5′-phosphate-dependent aminotransferases. Positions homologous to either the dialkylglycine decarboxylase or ornithine aminotransferase are boxed. The gaps in the ornithine aminotransferase-aspartate aminotransferase alignment were assigned by Mueckler and Pitot (1985). [1]This work; [2]Mueckler and Pitot (1985); [3]Degols, 1987; [4]Graf-Hauser et al. (1983); [5]Doonan et al. (1975); [6]Fortheringham et al. (1986); [7]Oda et al. (1987); [8]Tanase et al. (1979).

DETAILED DESCRIPTION OF PREFERRED EMBODIMENT

Figure 1:
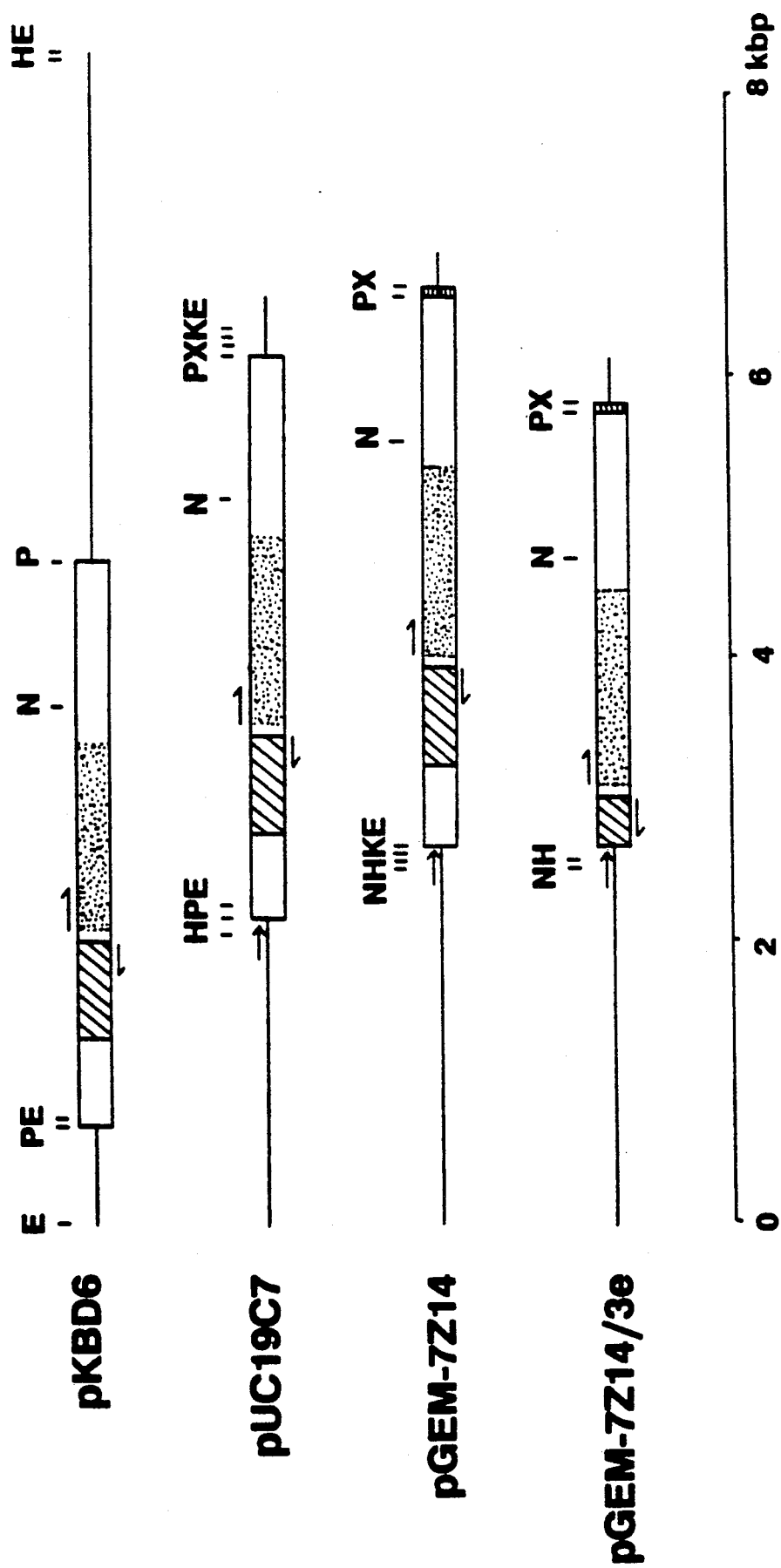
FIG. 1 depicts restriction maps of recombinant plasmids. Lines are vector DNA (pKBD6 is derived from pBR322, pUC19C7 from pUC19, and pGME-7Z14 from pGEM-7Zf(+), and boxes are inserts of P. cepacia DNA. Stippled region contains 2,2-dialkylglycine decarboxylase structural gene; angle-hatched region contains the putative repressor gene; horizontally hatched region contains a portion of the pUC19 multiple cloning site. Plasmid pGEM-7Z14/3e is 1 of 10 plasmids derived from pGEM-7Z14 that have a portion of the P. cepacia DNA deleted by exonuclease treatment. Restriction sites: E, EcoRI; P, PstI; N, NsiI, H, HindIII; K, KpnI; X, XbaI. Double-headed arrow, pUC19 lac promoter, single-headed arrows, direction of transcription of Pseudomonas genes.

The method of this invention will now be described in greater detail. This invention relates to a cloned repressor gene, a cloned expression system, and a process for expressing a gene.

Generally, a gene to be expressed can be inserted into a cloning vector in many ways. The nucleic acid fragment to be ligated can have cohesive ends compatible with any combination of sites in the vector. Alternatively, the nucleic acid fragment can have one or more blunt ends that can be ligated to corresponding blunt ends in the cloning sites of the vector. The nucleic acid fragment to be ligated can be further processed, if desired, by successive exonuclease deletion.

In the event that the nucleic acid fragment to be ligated does not contain a desired combination of cohesive ends, the fragment can be modified by adding a linker, an adaptor, or homopolymer tailing by one of three methods.

The first method involves the use of linkers, which are short pieces of double-stranded DNA of known nucleotide sequence. The linker, which contains a restriction site, can be ligated to the DNA molecules by using an excess quantity of the linker in the ligation reaction. Digestion of the resulting molecules with the appropriate restriction enzyme will cleave the linkers at the restriction sites to form the cohesive ends. The modified fragment is then ready for ligation into a vector having compatible cohesive ends.

The second method of attaching a cohesive end to a blunt-ended DNA molecule is through the use of adaptors, which are also short oligonucleotides. The adaptor has one blunt end and one cohesive end. The blunt end is ligated to the blunt ends of the DNA fragments to produce a new molecule with cohesive ends. Once again, the modified DNA fragment is then ready for ligation into a vector having corresponding cohesive ends.

The third method of producing cohesive ends on blunt-ended molecules involves homopolymer tailing. The homopolymer is a polymer in which all the subunits are the same. In order to ligate two tailed molecules, the homopolymers must be complementary. Thus, for example, poly(dG) tails can be attached to the vector and poly(dC) tails can be attached to the DNA fragment to be expressed. Base pairing between the two will occur when the molecules are mixed.

The expression vector employed in practicing this invention can be any double-stranded DNA molecule capable of transporting the nucleic acid fragment to be expressed into a host cell and capable of replicating within the cell. More particularly, the vector must contain at least one DNA sequence that can act as the origin of replication in a host cell. In addition, the vector must contain one or more sites for insertion of the nucleic acid sequence to be expressed. These sites will ordinarily correspond to restriction enzyme sites at which cohesive ends can be formed, and which are complementary to the cohesive ends on the nucleic acid fragment to be expressed. In general, this invention can be carried out with plasmid, bacteriophage, or cosmid vectors having these characteristics.

The vector can be introduced into the host cell using any technique appropriate for the specific vector. Examples such as transformation or transfection are well known in the art and protocols can be found in standard and widely available texts (Maniatis et al., 1982).

Restriction endonucleases employed in this invention are those that both recognize and cleave a DNA molecule at a specific sequence (Class II endonucleases). It is preferred that the restriction endonucleases employed in this invention be functionally pure; they should be substantially free of phosphatase contamination.

When a plasmid vector is used it is preferred that the plasmid carry one or more genes responsible for a useful characteristic, such as selectable marker, displayed by the host cell. Gene cloning strategies with plasmids often use a drug resistance marker to help locate bacterial colonies in which the genes have been cloned. In one type of strategy, plasmids having genes for resistance to two different drugs are chosen. For example, insertion of the DNA fragment of interest into a gene for an antibiotic inactivates the gene and destroys drug resistance. The second drug resistance gene is not affected when bacterial cells are transformed with the recombinants, and colonies containing the gene of interest can be selected by resistance to the second drug and susceptibility to the first drug.

Preferred antibiotic markers are genes imparting chloramphenicol, ampicillin, or tetracycline resistance to the host cell. It is preferred that antibiotic resistance be employed as the selectable marker to insure that the host cell in a culture contains the plasmid.

When a plasmid is employed, the plasmid can be derived from bacteria or some other organism or the plasmid can be synthetically prepared. The plasmid can replicate independently of the host cell chromosome or an integrative plasmid (episome) can be employed. The plasmid can make use of the DNA replicative enzymes of the host cell in order to replicate or the plasmid can carry genes that code for the enzymes required for plasmid replication. A number of different plasmids can be employed in practicing this invention. Typical of the plasmids that can be utilized are pBR322, pBR325, ColE1, RP4, pUC19, and the 2 $\mu$m circle that occurs in many strains of the yeast Saccharomyces cerevisiae.

The cloning vehicle can also be a bacteriophage, which is also referred to herein as a phage. The phage can have a head and tail structure or the phage can be characterized by a filamentous structure. It will be understood that this invention can be practiced with phage vectors that proliferate by lytic or by lysogenic infection.

Cloning and expression can be carried in procaryotic or eucaryotic cells. The host will of course be one that is compatible with the vector and the proteins that are expressed. Cloning and expression are preferably carried out in bacterial or yeast cells, although cells of fungal, animal, and plant origin can also be employed. The preferred host cells are bacterial cells, such as E. coli, as well as species of Bacillus and Pseudomonas. The use of E. coli cells is particularly preferred because bacterial plasmids and bacteriophages replicate in these cells.

The process of this invention can be carried out as a batch or as a continuous fermentation. The term "continuous fermentation" is used in its usual sense and means that nutrients are fed to a fermenter substantially continuously and that an output, or effluent, stream is substantially constantly withdrawn from the fermenter. The nutrient stream usually comprises an aqueous organic substrate solution. The effluent stream comprises biomass and the liquid phase from the fermentation medium. The term "batch fermentation" is also used in its conventional sense and refers to fermentation without continuous inflow and outflow.

Fermentation can be carried out in a bioreactor, such as a chemostat, tower fermenter or immobilized-cell bioreactor. Mixing can be supplied by an impeller, agitator or other suitable means and should be sufficiently vigorous that the vessel contents are of substantially uniform composition, but not so vigorous that the microorganism is disrupted or metabolism inhibited.

The identity of the chemical constituents in the nutrient medium and the amount of each constituent should be sufficient to meet the elemental requirements for cell mass and should supply appropriate energy for cell maintenance. The nutrient medium should contain sources of carbon, nitrogen, potassium, phosphorus, sulfur, magnesium, calcium, and iron in required amounts. The chemical constituents should also meet specific nutritional requirements including vitamins and trace minerals. This invention will now be described in greater detail with reference to a specific preferred embodiment.

The cloning and sequencing of the structural gene of the P. cepacia 2,2-dialkylglycine decarboxylase was undertaken to establish whether this enzyme is structurally and evolutionarily more closely related to the B-6-dependent decarboxylases than to aminotransferases. It is reported here, among other things, (i) the sequence of a cloned 3969-bp segment of P. cepacia DNA containing the 2,2-dialkylglycine decarboxylase structural gene, (ii) purification of the recombinant decarboxylase, (iii) determination of the amino acid sequence of the amino terminus and the active site peptide, and (iv) alignment of the deduced amino acid sequence of the deduced amino acid sequence of this decarboxylase with various aminotransferases.

Cloning—Isolation of the dialkylglycine decarboxylase gene was simplified by the inability of E. coli to metabolize 2,2-dialkylglycines. Thus, a library was created by ligating PstI-restricted P. cepacia DNA into the PstI site of pBR322 was screened for the dialkylglycine decarboxylase gene by plating the transformation mixture on LB/tetracycline agar to select transformants and subsequently making a replica transfer to 2-methylalanine/glucose agar. Isolated from one of several colonies that survived the transfer was a 16-kbp (kilobase pairs) recombinant plasmid containing several heterologous PstI fragments. A PstI digest of the plasmid was subcloned back into PstI-cut pBR322 and a pair of smaller recombinant plasmids, pKBD6 and PKBD14, were isolated; these were shown by restriction analysis to differ only in the orientation of a 4.0-kbp insert (FIG. 1). The 4.0-kbp PstI-PstI fragment was transferred into pUC19 to give pUC19C7 and the slightly smaller XbaI-EcoRI fragment of pUC19C7 (sequencing later showed that the EcoRI site is 77 bases away from the end of the insert) was transferred into pGEM-7Zf(+) to give pGEM-7Z14 (FIG. 1). E. coli transformed with plasmid pUC19C7 has been deposited at the American Type Culture Collection, Rockville, Md. 20852, under Accession No. 669010. Also, pUC19H1 was constructed from pUC19C7 by deletion of a 1.3-kbp SphI fragment (not shown). All the above recombinant plasmids, pKBD6, pKBD14, pUC19C7, pUC19H1, and pGEM-7Z14, confer on E. coli hosts the ability to grow on 2-methylalanine/glucose agar.

DNA Sequence—Sequencing was carried out using a modified Sanger dideoxy method (Sanger et al., 1977; Kraft et al, 1988). The (+)-strand of the insert (the upper strand in FIG. 1 and lower strand in FIG. 2; the coding strand for the decarboxylase structural gene) was sequenced using a 20-mer primer complementary to pGEM-7Z sequences on the left side of the insert and, as templates, plasmids with progressively larger deletions from the left. The − strand of the insert (the lower strand in FIG. 1 and upper strand in FIG. 2; the coding strand for the putative repressor gene) was sequenced using a 20-mer primer complementary to pUC19 sequences on the right side of the insert and, as templates, plasmids with progressively larger deletions from the right. One hundred percent of the control and structural genes was sequenced on both strands; 90% of the remaining sequence was determined on both strands. The 3969-nucleotide sequence is shown in two segments. FIG. 3 shows the 3′ end of the (+)-strand that contains the decarboxylase structural gene; FIG. 4 shows the 3′ end of the (−)-strand that contains the control gene. The cloned fragment contains 68% G+C, which is similar to the 65-68% G+C observed in various Pseudomonas species (Sober, 1968).

Figure 5:
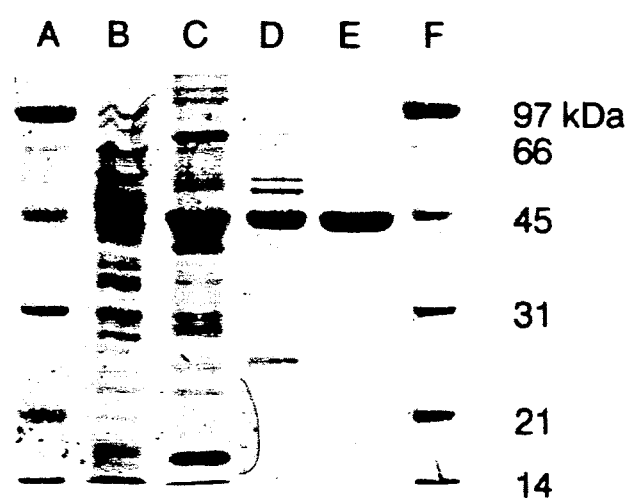
FIG. 5 shows SDS polyacrylamide gel electrophoresis of recombinant 2,2-dialkylglycine decarboxylase at various stages of purification. Lanes A and F, BioRad MW standards; B, sonicate supernatant; C, Butyl-TSK wash D, DEAE 5-PW active fraction; E, size exclusion active fraction.

Enzyme Expression and Purification—The recombinant decarboxylase was purified from E. Coli JM 109 carrying pGEM-7Z14/8b, a truncated derivative of pGEM-7Z14 with 1332 base pairs deleted from the left end leaving 63 nucleotides ahead of the decarboxylase gene. In this and other pGEM-7Z14 derivatives, the vector lac promoter lies upstream of and points toward the dialkylglycine decarboxylase gene (FIG. 1). When carbenicillin and IPTG were added to the JM109/pGEM-7Z14/8b growth medium, the dialkylglycine decarboxylase comprised about 0.5% of the cell extract, similar to levels induced by 2-methylalanine in Pseudomonas (Keller and O'Leary, 1979; Sato et al., 1978). The decarboxylase was purified from JM109/pGEM7Z14/8b in three steps using ammonium sulfate precipitation, ion exchange chromatography, and FPLC ion exchange chromatography. The purified enzyme was homogeneous as judged by SDS polyacrylamide gel electrophoresis (See Table 1 and FIG. 5).

RESULTS

TABLE 1

| Purification of Recombinant 2,2-Dialkylglycine Decarboxylase | | | | |
|---|---|---|---|---|
| | Protein (mg) | Total $U^a$ | $U^a$/mg protein | Yield (%) |
| Cell Sonicate | 260. | 1710 | 8.6 | 100 |
| Butyl-TSK | 4.8 | 710 | 148. | 42 |
| DEAE-5PW | 0.201 | 669 | 3400 | 39 |
| 300SW | 0.126 | 306 | 2430 | 18 |

$^a$One Unit = 1 nanomole $CO_2$ per min at pH 7.90 and 25° C.

Sequence of the Amino Terminus—The purified protein was sequenced at the amino terminus by automated Edman degradation. The results are included in FIG. 3. In the 14 cycles in which the phenylthiohydantoin-amino acid yields were high enough to make clear identifications, the experimentally determined residues matched the predicted ones. This sequence also shows that the decarboxylase terminal N-formylmethionine has been removed, but no additional amino-terminal proteolysis has occurred.

Figure 6:
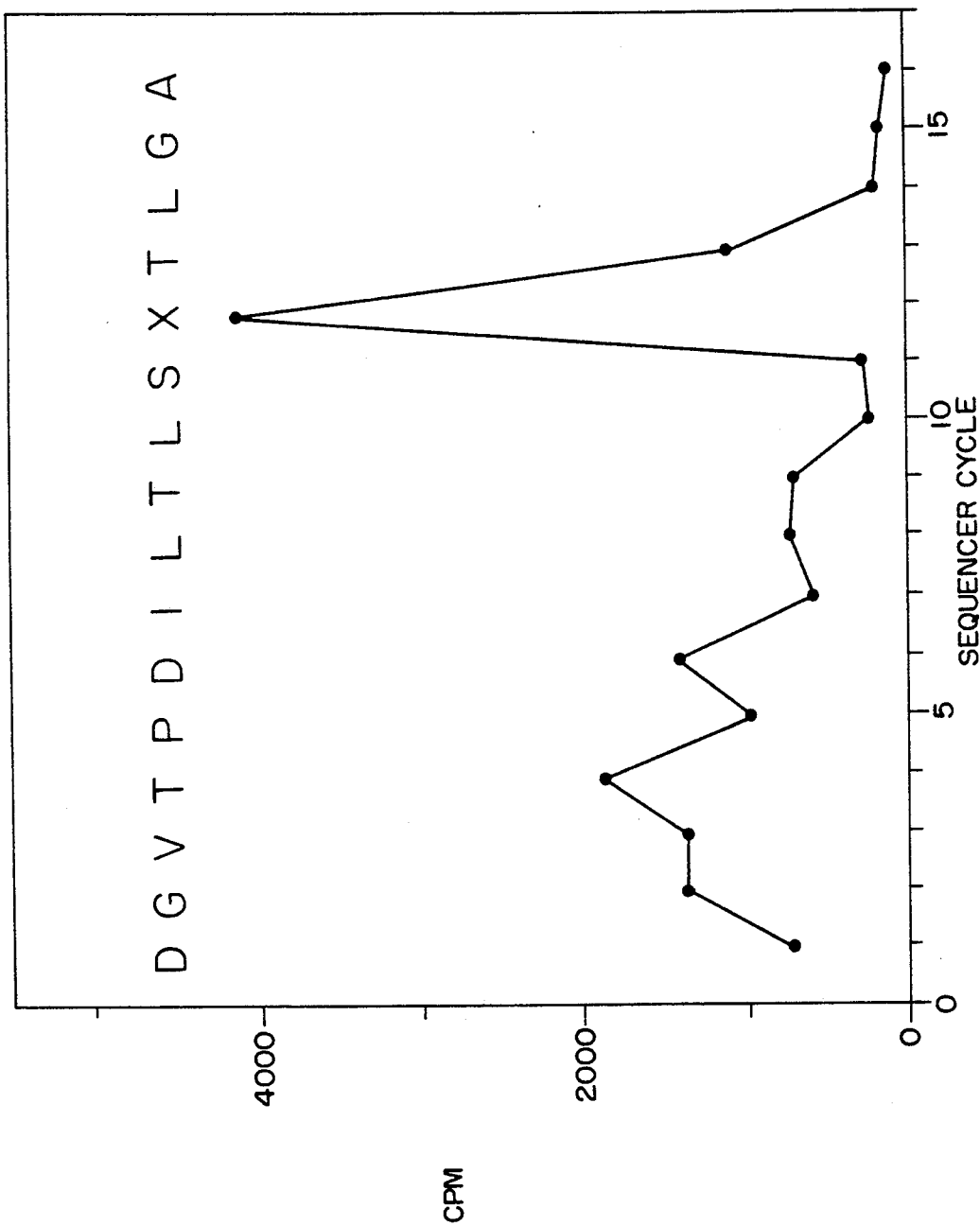
FIG. 6 depicts radioactivity released with each sequencer cycle during sequencing of the $^3$H-pyridoxal 5′-phosphate-labeled tryptic peptide.

Sequence of the Active Site Peptide—The decarboxylase active site was labeled using a variation of the method first introduced by Fischer et al. (1958). In this procedure, the active site lysine-[4′-$^3$H]pyridoxal 5′-phosphate imine bond of the holoenzyme was reduced with sodium borohydride. The labeled active site peptide was isolated by trypsin digestion followed by reversed phase high performance liquid chromatography separation of the resulting peptides. The major radioactive peptide was sequenced, and the amount of radioactivity released by each cycle of the automated Sequencer was determined. Sixteen cycles were clearly identifiable: all except cycle 12 agreed with the predicted amino acid sequence beginning after R260. Cycle 12 produced the most radioactivity and showed no identifiable peak on the Sequencer (see FIG. 6). This is presumably the cofactor-labeled lysine residue predicted by the DNA sequence.

Figure 2:
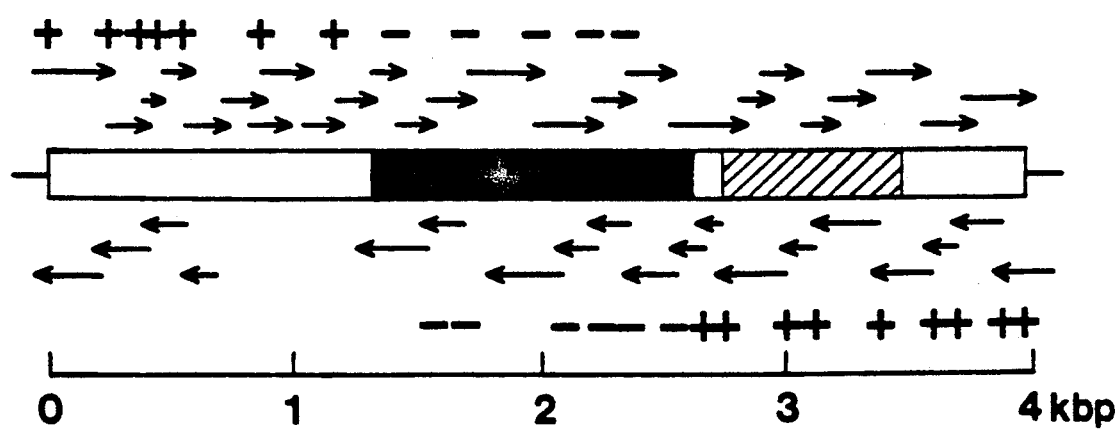
FIG. 2 describes sequencing strategy and growth characteristics of partially deleted plasmids on 2-methylalanine/glucose agar. Arrows begin at the last base of each partially deleted plasmid and point as far as sequence was determined. Arrows above the box refer to unidirectional deletions from pUC19C7; arrows below the box refer to unidirectional deletions from pGEM-7Z14. JM109 carrying a plasmid deleted to the (+) symbol forms large colonies on 2-methylalanine/glucose agar; JM109 carrying a plasmid deleted to the (−) symbol does not grow on 2-methylalanine/glucose agar. The 2,2-dialkylglycine decarboxylase structural gene is on the lower strand in the solid region; the putative repressor gene is on the upper strand in the cross-hatched region.

Identification of the Dialkylglycine Decarboxylase Structural Gene—The ATG initiation codon of the 1302-base dialkylglycine decarboxylase structural gene is at position 1395 of the (+)-strand of the insert (FIGS. 1-3). This ATG marks the beginning of the only large reading frame within the region of the insert that is necessary for expression of decarboxylase activity. The predicted amino acid sequence of this coding region matches the experimentally determined sequences at the amino terminus and active site.

Ahead of the structural gene, a CCGGAG sequence was found that is similar to the ribosome binding sites ahead of other bacterial genes (Min et al., 1988; Stormo et al., 1982). Also, 40 nucleotides downstream of the TAA stop codon is a 31-base GC-rich sequence with dyad symmetry that could form a 12-base stem, 7-base loop structure. The sequence immediately downstream of this dyad is not T-rich; thus, this sequence is similar to σ-dependent transcription terminators in other bacterial operons (Platt, 1986).

Codon usage within the decarboxylase coding region is strongly biased toward codons with G or C in the third position: 401 out of 434 codons (92%) have G or C in the third position (Table 2).

TABLE 2

Codon Usage in the *Pseudomonas cepacia*
Dialkylglycine Decarboxylase Gene Nucleotides
1395-2699

| | | | | | | | | | | | |
|---|---|---|---|---|---|---|---|---|---|---|---|
| TTT | Phe | 0 | TCT | Ser | 0 | TAT | Tyr | 3 | TGT | Cys | 0 |
| TTC | Phe | 15 | TCC | Ser | 4 | TAC | Tyr | 9 | TGC | Cys | 6 |
| TTA | Leu | 0 | TCA | Ser | 0 | TAA | — | 1 | TGA | — | 0 |
| TTG | Leu | 2 | TCG | Ser | 10 | TAG | — | 0 | TGG | Trp | 2 |
| CTT | Leu | 0 | CCT | Pro | 0 | CAT | His | 1 | CGT | Arg | 0 |
| CTC | Leu | 27 | CCC | Pro | 5 | CAC | His | 6 | CGC | Arg | 25 |
| CTA | Leu | 0 | CCA | Pro | 1 | CAA | Gln | 0 | CGA | Arg | 1 |
| CTG | Leu | 21 | CCG | Pro | 13 | CAG | Gln | 8 | CGG | Arg | 6 |
| ATT | Ile | 1 | ACT | Thr | 0 | AAT | Asn | 0 | AGT | Ser | 1 |
| ATC | Ile | 25 | ACC | Thr | 4 | AAC | Asn | 9 | AGC | Ser | 8 |
| ATA | Ile | 0 | ACA | Thr | 0 | AAA | Lys | 2 | AGA | Arg | 0 |
| ATG | Met | 13 | ACG | Thr | 18 | AAG | Lys | 9 | AGG | Arg | 2 |
| GTT | Val | 0 | GCT | Ala | 0 | GAT | Asp | 0 | GGT | Gly | 2 |
| GTC | Val | 16 | GCC | Ala | 11 | GAC | Asp | 21 | GGC | Gly | 36 |
| GTA | Val | 0 | GCA | Ala | 5 | GAA | Glu | 8 | GGA | Gly | 2 |
| GTG | Val | 12 | GCG | Ala | 33 | GAG | Clu | 16 | GGG | Gly | 9 |

This percentage is consistent with the prediction of Bibb et al. (1984) that 88% of the third positions will have G or C in a gene having 68% G+C. Codon bias analysis was particularly helpful in identifying the reading frame of the decarboxylase structural gene in this GC-rich DNA, since the non-coding reading frames are not nearly as biased toward G and C in the third position.

The length and amino acid content of the decarboxylase polypeptide deduced from the nucleotide sequence is nearly identical with that determined by Lamartiniere et al. (1971) for the dialkylglycine decarboxylase from another Pseudomonas isolate. A sequence identity of 83% is predicted for these two proteins using Cornish-Bowden's method based on amino acid content (Cornish-Bowden, 1979). Considering the possibility of error in the amino acid determination, it is likely that the enzyme studied in this work, which is the same one studied by Sato et al. (1978), is identical with the one studied by Lamartiniere et al. (1971).

Homology Searches—The deduced amino acid sequence of the *P. cepacia* dialkylglycine decarboxylase was compared with the Protein Identification Resource database (Release 17) and with translations of all six reading frames of each DNA sequence in the GenBank (Release 60) and the EMBL (Release 15) databases (Henikoff and Wallace, 1988). The GenBank search located three sequences that showed significant homology to the dialkylglycine decarboxylase; the 423-amino acid translation of yeast ornithine aminotransferase mRNA (Degois. 1987), and the 439 amino acid translations of rat (Mueckler and Pitot, 1985) and human (Mitchell et al., 1988) ornithine aminotransferase mRNAs. Comparison of these sequences with the deduced dialkylglycine decarboxylase sequence using a moving 30-amino acid window (Wilbur and Lipman, 1983) gives log odds scores of 10.5, indicating a significant sequence similarity (Henikoff and Wallace, 1988). No decarboxylase sequence scored higher than 9.8 in the search procedure and alignments of several decarboxylase sequences with the dialkylglycine decarboxylase sequence showed no noteworthy similarities. Homologies with other aminotransferases were weak except near active site lysines as discussed below. The *E. coli* branched chain aminotransferase (Inoue et al., 1988) and phosphoserine aminotransferase (van del Zel et al., 1989) showed no homology with the dialkylglycine decarboxylase or ornithine aminotransferase even in active site regions.

Figure 7:
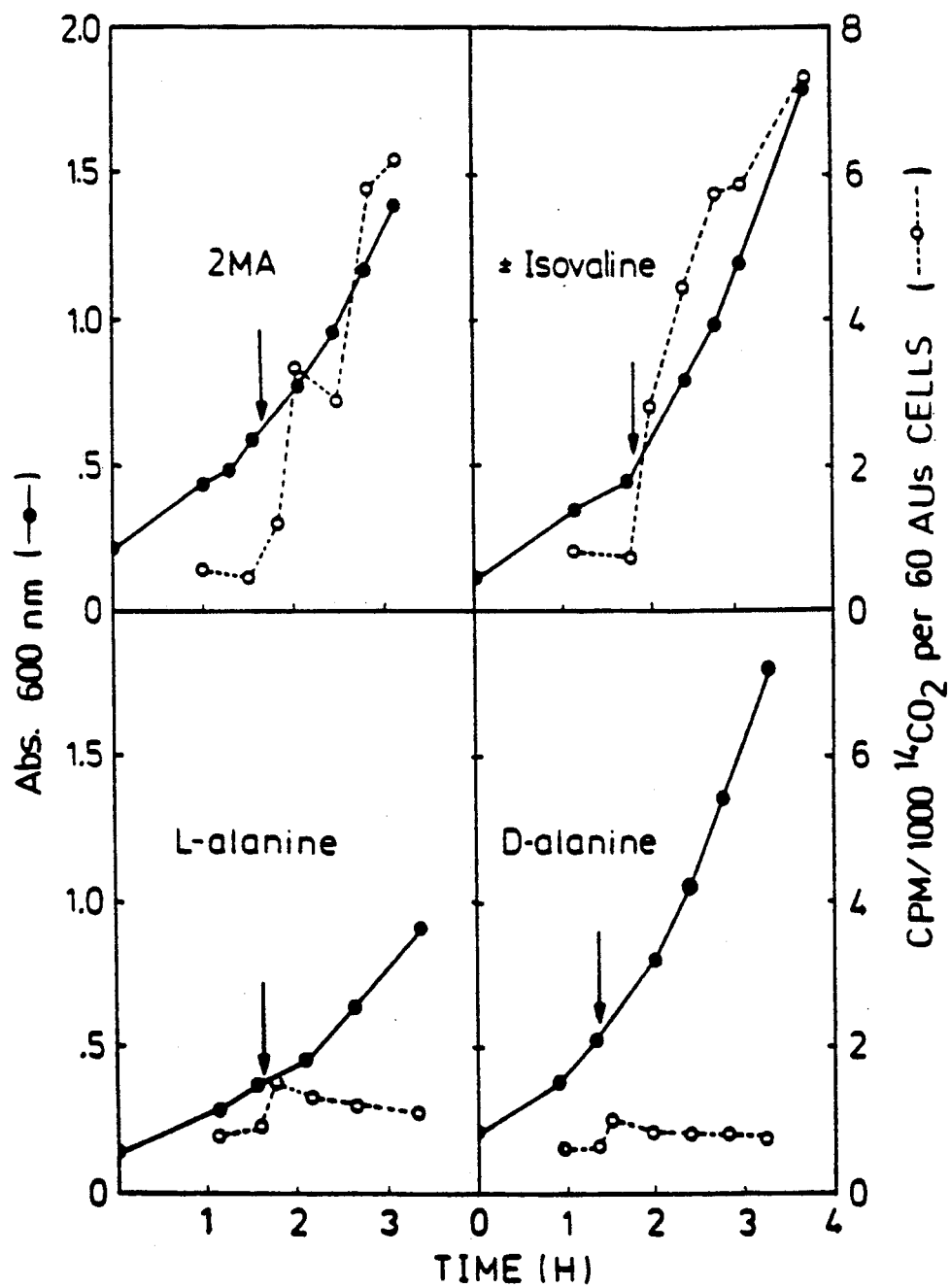
FIG. 7 depicts induction of dialkylglycine decarboxylase activity in E. coli DH5a/pKBD6 cultures by various amino acids. One-liter cultures containing minimal salts, glucose, NH$_4$Cl, and tetracycline (12 μg/ml) were supplemented at the indicated time with amino acid (final concentration, 10 mM). Absorbance of the culture was measured at 600 nm in a 1-cm cell (●—●). Each activity assay contained 60 absorbance units of resuspended bacteria (○—○).

Dialkylglycine Decarboxylase Gene Induction—The kinetics of decarboxylase induction in *E. coli* host DH5a carrying plasmid pKBD6 were studied with several amino acids that are substrates for the dialkylglycine decarboxylase and that therefore might be expected to be gene inducers. These are racemic isovaline, 2-methylamine, and D-alanine, which are decarboxylated by the enzyme, and L-alanine, which is transaminated (Bailey et al., 1970). As shown in FIG. 7, when DH5a/pKBD6 was grown in minimal media containing ammonium chloride as nitrogen source, decarboxylase specific activity was low. Addition of either 2-methylalanine or racemic isovaline caused an immediate and rapid increase in decarboxylase specific activity, approximately paralleling growth. Decarboxylase production ceased with growth and remained stable for several hours in the induced cells (data not shown). In contrast, when D- or L-alanine was added to growing cell cultures, no decarboxylase production ensued.

Induction Stereochemistry—The induction phenomenon was further investigated by surveying the inducing ability of the separate isovaline stereoisomers and 15 other structurally similar amino acids (Table 3). JM109/pGEM7Z14 was grown overnight in YT-ampicillin plus 20 mM amino acid, then cell sonicate supernatants were assayed for protein and dialkylglycine decarboxylase activity. The assays showed decarboxylase specific activities 10 times the untreated control only if S-isovaline, 2-methylalanine, or L-2-aminobutanoic acid had been added to the culture medium; 1-aminocyclopentanecarboxylic acid induced an intermediate level. The other amino acids tested induced no better than the culture medium itself.

Figure 8:
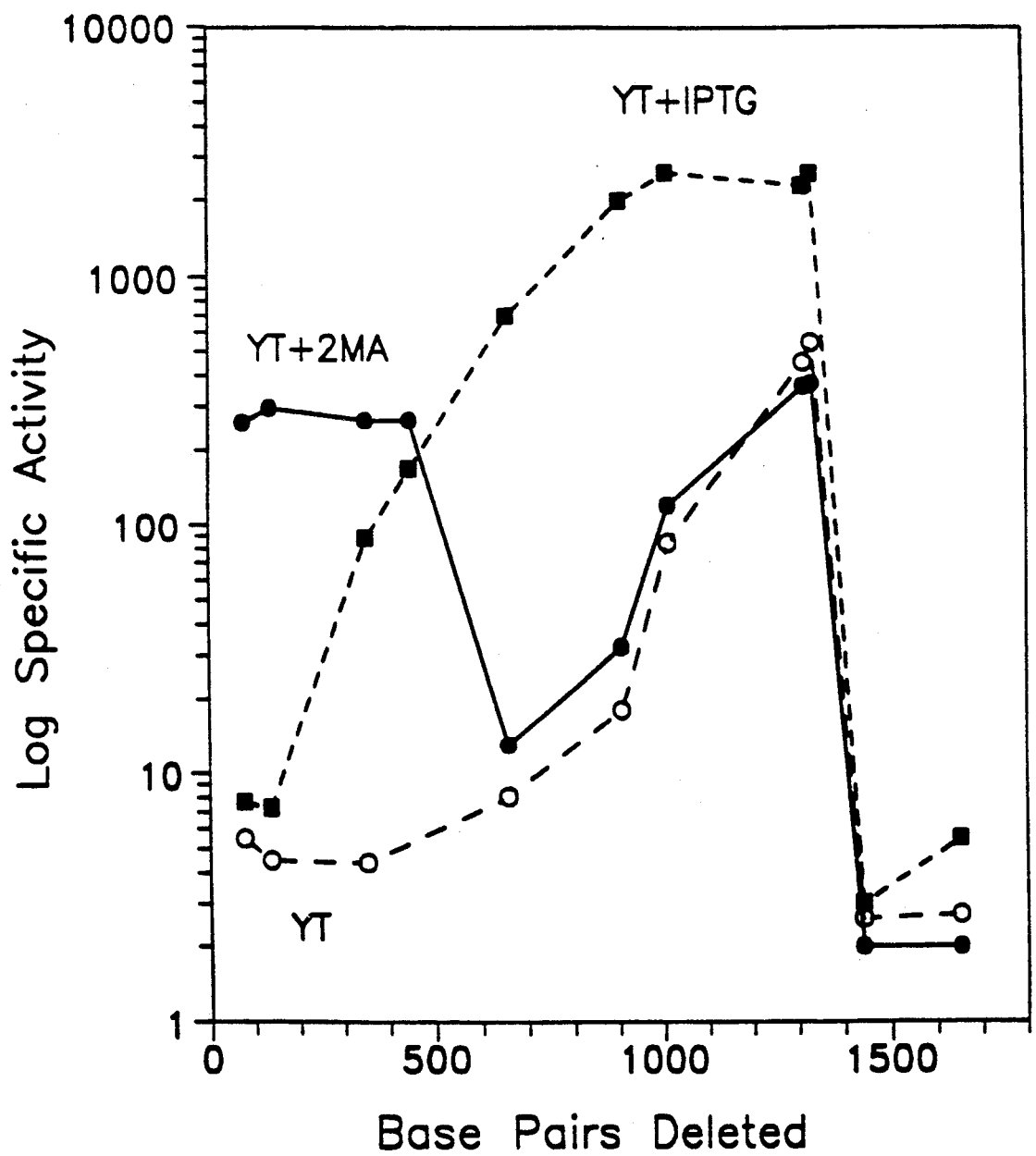
FIG. 8 shows dialkylglycine decarboxylase specific activity in extracts of E. coli JM109 carrying pGEM-7Z14 or a derivative with up to 1651 bp deleted. Cultures were grown over night in YT medium (○—○), YT plus 20 mM 2-methylalanine (●—●), or YT plus 1 mg/ml IPTG (■—■). Units of nmol h$^{-1}$ mg$^{-1}$.

The role of the upstream DNA in controlling decarboxylase gene expression was investigated by determining decarboxylase levels in *E. coli* JM109 carrying PGEM-7Z14 or one of 10 plasmids derived from it with various lengths of insert removed by exonuclease treatment. In these constructs, transcription from the vector lac promoter, which is upstream of the insert and pointing toward it, was controlled by maintaining the plasmids in host strain JM109, an overproducer of the lac repressor (Yanisch-Perron et al., 1985). FIG. 8 shows decarboxylase specific activities of the various JM109 strains grown in YT, YT plus 2-methylalanine, or YT plus IPTG. Most obviously, truncation by 1440 or 1651 bp completely prevented production of active dialkylglycine decarboxylase under all growth conditions. These deletions removed part of the decarboxylase structural gene that has been shown by sequencing to begin at 1395 of the insert. In the presence of IPTG, the strains carrying the next two larger plasmids (1332 and 1314 bp removed) produced high levels of enzyme, about 500-fold over background. When grown in untreated or 2-methylalanine-treated medium, these latter strains produced decarboxylase levels about 30-fold over background. Strains carrying the next three larger plasmids (1012, 907, and 658 bp removed) produced much less decarboxylase activity with or without 2-methylalanine, while the IPTG-induced levels in all three remained over 100 times background. Finally, in strains carrying the four largest plasmids (447, 352, 137, and 77 bp removed from the original insert), 2-methylalanine induced enzyme activities jumped back to 30 times the untreated levels, while the effect of IPTG decreased to nil.

DISCUSSION

Figure 9:
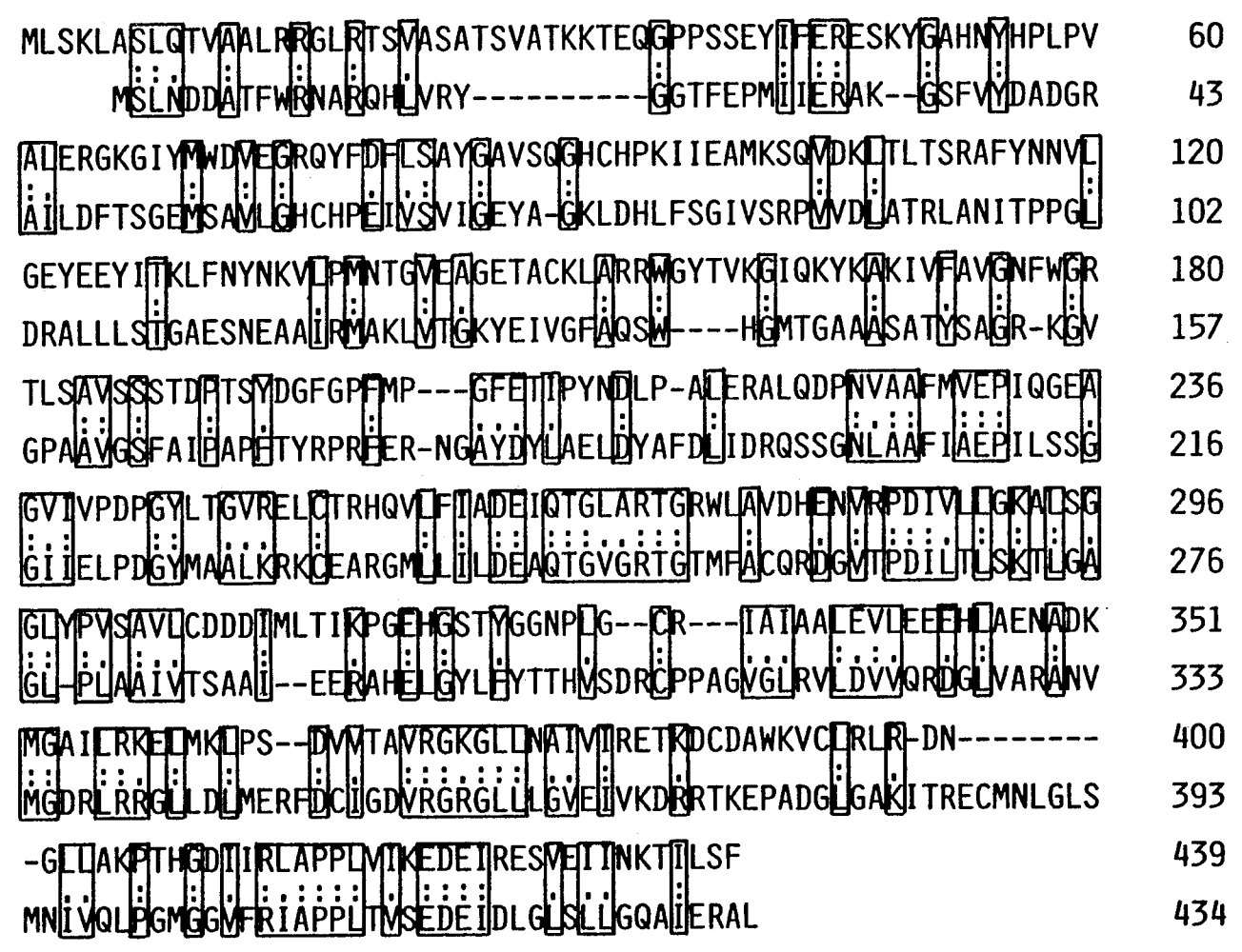

Alignment of the deduced amino acid sequences of P. cepacia 2,2-dialkylglycine decarboxylase and rat ornithine aminotransferase is shown in FIG. 9. The overall homology between these sequences is 24%; however, most of the homologous segments are in the 230-amino acid carboxyl termini: in this region, 56% of the residues are homologous. This region of ornithine aminotransferase is homologous with the carboxyl terminus of aspartate aminotransferase (Mueckler and Pitot, 1985) that, as shown by X-ray crystallography, contains the cofactor binding domain (Ford et al., 1980: Graf-Hausner et al., 1983: Borisov et al., 1980; Kagamiyama et al., 1980). Thus, although direct alignment of dialkylglycine decarboxylase and aspartate aminotransferase sequences shows little sequence similarity, it is likely that the carboxyl termini of both the decarboxylase and ornithine aminotransferase form the major part of pyridoxal 5'-phosphate binding pockets.

The yeast ornithine aminotransferase sequence shows a 14% homology with the dialkylglycine decarboxylase sequence (and is only 50% homologous with the rat or human sequences) (Deois, 1987). The regions of major similarity are around the active site lysines.

The optimum overall alignment of the dialkylglycine decarboxylase and rat ornithine aminotransferase sequences (FIG. 9) aligns only one pair of lysines, K272 of the former and K292 on the latter. Simmaco et al. (1986) have shown that K292 is at the active site of ornithine aminotransferase, while we have shown that K272 is the active site lysine in the dialkylglycine decarboxylase. The amino acid sequences on either side of these lysines are also conserved in several other aminotransferases as shown in FIG. 10. One sequence in particular seems strongly conserved besides the active site lysines: this is a DIVL box six to nine amino acids on the amino side of the lysines. The crystal structure of the chicken mitochondrial AAT shows these residues in one strand of the seven-strand pleated sheet that forms the back wall of the cofactor binding site (Jansonius et al., 1985).

A surprising finding was the lack of an active site histidine-lysine pair in the 2,2-dialkylglycine decarboxylase. All known procaryotic pyridoxal phosphate-dependent decarboxylases, including E. coli arginine, lysine, ornithine, and glutamate decarboxylases (Tanase et al., 1979) and two eucaryotic decarboxylases, the pig kidney L-$\beta$-3,4-dihydroxyphenylalanine decarboxylase (Tanase et al., 1979) and Morganella morganii histidine next to the active site lysine that can be partially assumed by glutamine (Vaaler and Snell, 1989). Sato et al. (1978) found that diethyl pyrocarbonate modifies one of seven histidines of the dialkylglycine decarboxylase, inhibiting the decarboxylation reaction selectively. Thus, this enzyme probably still requires the histidine catalyst, but it is elsewhere in the active site instead of adjacent to lysine.

Maximum levels of dialkylglycine decarboxylase expression from these plasmids in E. coli was similar to that in 2-methylalanine-induced P. cepacia (Keller and O-Leary, 1979; Lamartiniere et al., 1971). Steps were taken to maximize expression of the cloned decarboxylase gene by orienting the gene downstream of the strong inducible lac promoter and removing (in pGEM-7Z14/8b) all but 76 base pairs (bp) of cloned DNA upstream of the structural gene. We ascribe the low expression levels to translational barriers. Slow translation could be caused by several arginine codons, namely CGA, AGG, and CGG that are associated with genes weakly expressed in E. coli (Bulmer, 1988). These codons occur, respectively, one, twice, and six times in the decarboxylase structural gene. Another translational barrier could be a ribosome binding sequence that is non-optimal for E. coli. Recent studies have shown that in E. coli the mRNA ribosome binding site occupies positions -13 to -8 relative to the initiation codon and has a consensus sequence of AAGGAG (Min et al., 1988; Stormo et al., 1982) whereas that site ahead of the dialkylglycine decarboxylase gene has the sequence CCGGAG.

Control of decarboxylase gene expression is probably exercised by an upstream repressor gene. The repressor gene was located by decarboxylase gene induction experiments with strains carrying plasmids with the Pseudomonas DNA inert truncated by various amounts (FIG. 8). pGEM-7Z14 and the next three smaller plasmids (from 77 to 447 bp of the insert removed) all show complete repression of decarboxylase gene expression in the absence of 2-methylalanine and complete derepression by 2-methylalanine. Thus, the control system is intact and identical in these four plasmids. Truncation by another 211 bp (658 bp total) results in a dramatic lowering of decarboxylase expression to the background level even in the presence of 2-methylalanine. This 658-bp shortening removes 10 codons from the 3' end of the repressor coding region, with the removed DNA probably encoding all or part of a 2-methylalanine-binding domain at the repressor's carboxyl terminus. The portion of the gene coding for the repressor's DNA binding domain is left untouched in this plasmid and is likely still transcribed from a promoter at the other end. The resulting shortened or modified protein could still bind to an operator sequence, but would no longer be affected by 2-methylalanine. Truncation by 907 or 1012 bp results in partial repression of decarboxylase expression, which probably is due to synthesis of portions of the DNA binding domain that retain some affinity for the operator site. Finally, removal of 1314 or 1332 bp abolishes all repression by removing all or most of the DNA coding for the DNA binding domain, but still leaves a promoter on both plasmids just ahead of the decarboxylase gene. Expression levels from these latter plasmids are identical with the 2-methylalanine induced levels observed with the larger plasmids, as expected if RNA polymerase had unrestricted access to the Pseudomonas dialkylglycine decarboxylase promoter. While the results indicate that the decarboxylase promoter is within 75 nucleotides of the structural gene, its precise location and sequence have not been established; there are no clear sequence homologies with known Pseudomonas or E. coli promoters.

IPTG-induced decarboxylase gene expression was greater the closer the lac promoter was to the decarboxylase gene (FIG. 8). In pGEM-7Z14 and the next smallest plasmid, transcription from the lac promoter is weak enough that it can be completely blocked by the dialkylglycine decarboxylase repressor. As the intervening DNA is shortened, which may remove transcription-terminating sequences, repressor binding only partially blocks read-through from the lac promoter. Expression was highest when the lac-decarboxylase separation was 500 bp or fewer.

The most likely candidate for the repressor gene is a 687 nucleotide region beginning 81 bases upstream from the decarboxylase structural gene and coding for a 229-amino acid protein (FIGS. 1 and 4). This coding region extends 30 bp past the truncation site that destroys the repressor's sensitivity to 2-methylalanine (FIG. 8). The gene product is predicted to be basic, containing 20% arginine plus lysine. This composition is similar to the eucaryotic histones H3 and H4. Just ahead of this reading frame (-14 to -6 relative to its ATG start codon) is a ribosome binding site for translation of the repressor mRNA. No significant sequence similarities between the amino acid sequence predicted for this repressor and any of the translated reading frames of the GenBank DNA sequence (Henikoff and Wallace, 1988) could be found.

The stereochemical characteristics of the amino acid binding site responsible for modulating DNA binding are apparent in Table 3.

ents; for example, two methyls as in 2-methylalanine or an ethyl on one side and a hydrogen on the other side as in 2-aminobutanoic acid. These groups would provide a minimum hydrophobic interaction energy with the repressor binding site. Only 2-methylalanine, S-isovaline, and L-2-amino-butanoic acid satisfy these criteria. 1-Aminocyclopentanecarboxylic acid is a weak inducer, perhaps fitting portions of its ring β-methylenes into both alkyl group binding sites.

The stereospecificity of dialkylglycine decarboxylase gene induction by isovaline is opposite that of the decarboxylase. Asalestad et al. (1968) reported that the Michaelis constants of the R and S isomers are 1.0 mM and 25 mM, respectively. And relative $V_{max}/K_m$ values, which correlate with affinity of the enzyme for the transition state of the decarboxylation reaction are 7.9 and 1.0 for R and S isomers, respectively. Sterically, the enzyme is more flexible than the repressor: it decarboxylates several amino acids that do not induce decarboxylase gene expression, including D-alanine (Bailey et al., 1970), racemic 2-methylnorvaline (Tahara et al., 1969), and 1-aminocyclo-pentanecarboxylic acid. Also, several other amino acids are decarboxylase substrates but have not been tested for gene induction, including 1-aminocyclobutanecarboxylic acid, 2-amino-2-ethyl-butanoic acid, and racemic 2-methylserine.

Another surprising stereochemical consequence of these results is that the only known biological sources of isovaline, the so-called peptaibol antibiotics of soil fungi, contain R-isovaline and not S-isovaline (Bosch et al., 1982). Thus, it is unlikely that the dialkylglycine decarboxylase genes studied here have evolved specifi-

TABLE 3

2,3-Dialkylglycine Decarboxylase Structural and Control Genes
Induction of cloned dialkylglycine decarboxylase
activity by alky-substituted amino acide [C(pro-R)
(pro-S)(NH$_2$)(COOH)]

| Amino Acid | pro-R | pro-S | Specific activity nmol h$^{-1}$ mg$^{-1}$ | S.D. (No. of experiments) |
|---|---|---|---|---|
| Control | | | 5.12 | 4.01 (14) |
| Glycine | H | H | 5.20 | 0.20 (2) |
| L-Alanine | H | CH$_3$ | 1.74 | 0.20 (2) |
| L-2-Aminobutanoic acid | H | CH$_2$CH$_3$ | 48.8[b] | 12.00 (4) |
| L-Norvaline | H | CH$_2$CH$_2$CH$_3$ | 4.51 | 0.08 (2) |
| L-Valine | H | CH(CH$_3$)$_2$ | 4.22 | 0.16 (2) |
| L-Isoleucine | H | CH(CH$_3$)CH$_2$CH$_3$ | 4.05 | 0.29 (2) |
| D-Alanine | CH$_3$ | H | 3.76 | 0.20 (2) |
| D-2-Aminobutanoic acid | CH$_3$CH$_2$ | H | 2.56 | 0.08 (2) |
| D-Norvaline | CH$_3$CH$_2$CH$_2$ | H | 4.21 | 0.08 (2) |
| D-Valine | (CH$_3$)$_2$CH | H | 4.59 | 0.25 (2) |
| D-Isoleucine | CH$_3$CH$_2$CH(CH$_3$) | H | 3.39 | 0.12 (2) |
| 2-Methylalanine | CH$_3$ | CH$_3$ | 58.7[b] | 22.70 (16) |
| S-Isovaline | CH$_3$ | CH$_2$CH$_3$ | 41.8[b] | 11.10 (4) |
| S-2-Methylnorvaline | CH$_3$ | CH$_2$CH$_2$CH$_3$ | 12.8 | 5.95 (4) |
| R-Isovaline | CH$_3$CH$_2$ | CH$_3$ | 6.45 | 1.45 (4) |
| R-2-Methylnorvaline | CH$_3$CH$_2$CH$_2$ | CH$_3$ | 5.45 | 1.20 (4) |
| 1-Aminocyclopentane carboxylic acid | CH$_2$CH$_2$ | CH$_2$CH$_2$ | 16.5[b] | 10.70 (4) |

[a]For duplicate experiments (n = 2), the average deviation is given.
[b]Greater than control at the 99% confidence level by the Mann-Whitney test.

These data suggest that the amino acid binding domain of the repressor incorporates sites for each α alkyl group, besides ionic sites for the α-NH$_3$+ and/or the α-COO−. One alkyl group binding site, the pro-R one, interacts with a pro-r methyl of the substrate, but is too small to accept larger alkyl groups. The other site, the pro-S one, binds either a pro-S methyl or ethyl, but nothing larger. Additionally, since neither glycine nor D- or L-alanine induce, an inducer of this gene must contain at least two methylene groups on the α substitucally to metabolize the isovaline occurring in peptide antibiotics. These genes and gene products more likely evolved to metabolize 2-methylalanine, which is achiral and is present in greater amounts than isovaline in the peptaibol antibiotics (Schmitt and Jung, 1985).

These results cannot be explained by operation of a positive control system, since decarboxylase expression returns to depressed levels once all or most of the control gene has been deleted. Nor is it likely that decarboxylase gene expression is controlled in trans from *E. coli* DNA, since (i) the host cannot metabolize dialkylglycines and therefore probably does not have receptors that bind both the dialkylglycines and certain sequences of exogenous DNA and (ii) de-repression is stereospecific and consistent, making the action of a nonspecific DNA binding protein unlikely. Control is not exercised by DNA downstream of the cloned dialkylglycine decarboxylase gene, since plasmids truncated in that region still show the repression-de-repression properties of the intact plasmid (data not shown). Finally, the rapid induction kinetics (FIG. 7) indicate that a direct process such as repressor release turns on decarboxylase gene expression, rather than a multiple step process requiring synthesis of other proteins.

This study has outlined evidence for the existence of a new repressor that is regulated by three closely related alkyl-substituted amino acids. While the function of this system closely parallels other classical repressor-gene pairs, the predicted sequence suggests that a unique protein structure is involved. It is also shown that the *P. cepacia* dialkylglycine decarboxylase has a unique structure that is not homologous to known amino acid decarboxylase sequences, but instead is closely related to the eucaryotic ornithine aminotransferases and other aminotransferases. Thus, it may be more properly described as a decarboxylating aminotransferase rather than an aminotransferring decarboxylase. It is likely that the in vivo function of this enzyme in Pseudomonas is to decarboxylate dialkylglycines, since enzyme production in Pseudomonas is stimulated by 2-methylalanine (Aaslestad and Larson, 1964).

In summary, a 3969-base pair PstI-PstI fragment of *Pseudomonas cepacia* DNA containing the gene for the pyridoxal 5'-phosphate dependent 2,2-dialkylgylcine decarboxylase (pyruvate) (EC 4.1.1.64) was cloned in *Escherichia coli*. The insert was sequenced by the dideoxy method using nested deletions from both ends, revealing a central 1302-base pair region that codes for the decarboxylase subunit. The recombinant enzyme was expressed in *E. coli*, purified to homogeneity, and sequenced at the amino terminus. Also, a cofactor-labeled active site peptide was sequenced. The carboxyl terminus of the deduced amino acid sequence is homologous with the carboxyl terminus of mammalian ornithine aminotransferase; the active site sequence is similar to the active site sequences of several other aminotransferases. No homologies with known decarboxylase sequences could be found. Expression of the decarboxylase gene is negatively controlled by a 687-nucleotide sequence upstream of and diverging from the structural gene. Expression is induced by S-isovaline, 2-methylalanine, and D-2-aminobutanoic acid, but not by glycine, D-or L-alanine, L-2-aminobutanoic acid, R-isovaline, or other alkyl amino acids.

Additional modifications will readily occur to those skilled in the art. One such modification would be to modify the expression vector making it useful for the regulated expression of other genes. Such a recombinant expression vector comprises a bacterial promoter, the nucleotide sequence of the invention coding for the repressor protein, a nucleotide sequence coding for a ribosome binding site, and a restriction endonuclease cleavage site for insertion of a foreign gene. In this vector, the promoter and the nucleotide sequence encoding the repressor protein are arranged for read through transcription by a polymerase, and the restriction endonuclease cleavage site is downstream from the ribosome binding site. As discussed, supra, such an expression system is derepressed by an inducer. The inducers of choice are S-isovaline, 2-methylalanine, L-2-aminobutanoic acid, or 1-aminocyclopentanecarboxylic acid. It is also possible to add a secondary prokaryotic promoter upstream from the gene to be expressed. A preferred secondary promoter would be the ac promoter. In this case the ac promoter is derepressed by IPTG. Thus, it is possible to control the expression of the recombinant protein by linducers for the indigenous (i.e. decarboxylase) promoter, the lac promoter, or both.

The repressor protein and the nucleotide sequence encoding the repressor protein of the invention are in concentrated form. By this it is meant that the repressor protein and nucleotide sequence are found in higher levels in the expression system of the invention than in *Pseudomonas cepacia* cells in which they naturally occur. The repressor protein and the nucleotide sequence encoding the protein can be obtained in purified form according to this invention. By this it is meant that the repressor protein and the nucleotide sequence are free of other proteins, nucleotide sequences, and other cell comonents of Pseudomonas cepacia strains in which they naturally occur.

A detailed description of the experimental procedures that can be employed in practicing this invention follows.

Experimental Procedures

Bacterial Strains and Media. For transformations with recombinant plasmids the *E. coli* strains used were MM294 (K-12, endA1, thi-1, hsdR17, supE44, $\alpha$-), DH5$\alpha$ (F−, endA1, hsdR17(r−$_k$ m+$_k$), supE44, thi-1, k-, recA1, gyrA96, relA1, $\phi$80dlacS$\Delta$M15], and JM109 (recA1, $\Delta$lac-pro, endA1, gyrA96, thi-1, hsdR17, supE44, [F':traD36, proAB+, lacI$^q$-Z$\Delta$M15]). A *Pseudomonas cepacia* strain obtained from Dr. M. Homma of the Department of Biochemistry, Hokkaido University, was the source of chromosomal DNA. This bacterial culture was clearly identified as *Pseudomonas cepacia* by the API 20E system (identification number 5-206-027-53) and other tests it has been deposited with the ATCC. *E. coli* strains were grown on LB medium or agar (Maniatis et al., 1982) containing ampicillin or carbenicillin at 50-100 mg/L or tetracycline at 12 mg/L. Selection and growth of clones coding for dialkylglycine decarboxylase was carried out on M9 minimal medium or agar (Maniatis et al., 1982) containing 1 g/L of ammonium chloride or 2-methylalanine as nitrogen source and the appropriate antibiotic. P. cepacia was grown on Difco nutrient broth (or agar) and minimal medium (or agar ((9.5 g/L $K_2HPO_4.3H_2O$, 3 g/L $KH_2PO_4$, 40 g/L glycerol, 87 mg/L $K_2SO_4$, 36 mg/L $MgCl_2.6H_2O$, and 2.8 mg/L $FeCl_3.H_2O$ with either 1 g/L $NH_4Cl$ or 2 g/L 2-methylalanine).

Recombinant DNA Techniques. Methods were as described by Maniatis et al. (1982). Restriction enzymes and T4 DNA ligase were obtained from Bethesda Research Laboratories, IBI or Promega and were used as recommended by the supplier. Competent cells were prepared by the calcium chloride or rubidium chloride/calcium chloride methods. (Golub, 1988; Maniatis et al. 1982).

Cloning and Subcloning of Pseudomonas DNA. Vector pBR322 was obtained in the *E. coli* strain MM294 as a gift from Dr. Milton Gordon; pUC19 and pGEM- 7Zf(+) DNAs were obtained from Bethesda Research Laboratories and Promega Corporation, respectively. Chromosomal DNA. was isolated from *Pseudomonas cepacia,* cut with PstI, and ligated to PstI-cut pBR322 DNA (K. B. Baurick, M. S. Thesis, University of Alaska Fairbanks, 1987) A ligation mixture containing 1 μg each of vector and insert was used to transform 200 μL of competent *E. coli* MM294, which was then transferred to 20 ml of LB medium. After 90 min. at 37° C. 50 μl aliquots of $10^{-1}$ dilution were plated on each of 22 100-mm LB/tetracycline plates. After 12h replica transfers were made to LB/carbenicillin and M9/2-methylalanine plates. After 60 h 5 adjacent colonies were observed on one M9/2-methylalanine plate. One colony was chosen for further study. Replating on appropriate media indicated a stable tet$^r$carb$^s$2MA+-phenotype. Transfer of the 4.0 kbp Pst I-Pst I fragment or related fragments to other vectors was carried out by ligation of appropriate restriction digests to the restricted vector, followed by host transformation, isolation of mini-prep plasmid DNA (Holmes and Quigley, 1981) and identification of the desired construct by restriction analysis.

Construction of Unidirectional Deletions. Deletions were made from either pUC19C7, pUC19H1, or pGEM-7Z14 by the method of Henikoff (Henikoff, 1984) using reagents and recommended procedures in the Promega Erasabase kit. Plasmid DNA for the deletion reactions was purified from minipreparations (Holmes and Quigley, 1981). Leftward deletions from the right end of the 4.0 kbp insert (FIG. 1) were made in both pUC19C7 and pUC19H1 by initially restricting with Kpn I and XbaI within the multiple cloning site. These enzymes were chosen because they do not cut within the Pseudomonas DNA insert and because they create ends which are respectively exonuclease III-resistant and exonuclease III-sensitive. The double-cut DNA was then digested with exonuclease III, aliquots were quenched at timed intervals, and the blunted ends ligated. The trimmed plasmids were isolated from hosts transformed with each ligation mixture and were characterized by restriction analysis. Rightward deletions from the left end of the insert in pUC19C7 (FIG. 1) could not be made because the appropriate pair of restriction sites are not available there. Thus, pGEM-7Z14 was constructed by transfer of a Xba I-Eco RI fragment from pUC19C7 to pGEM-7Zf(+); the new construct, pGEM-7Z14, contains three unique sites on the left side which create exonuclease III-resistant and exonuclease III-sensitive ends. This plasmid was cut with Eco RI and Kpn I or with Eco RI and Bst XI to generate the exonuclease III substrate, and then was treated as above.

DNA Sequencing. Sequence was obtained by the modified Sanger method as overlapping 100 to 300-base segments on both + and − strands using reagents and protocols recommended by suppliers of Sequenase (US Biochemicals) or Klenow enzyme (Boehringer). Template DNA was prepared by alkaline denaturation of miniprep DNA (Kraft, et al., 1988). Primers were synthesized by Synthetic Genetics, Inc., La Jolla, Calif. on an Applied Biosystems, Inc. Model 380 Synthesizer and were used without further purification. For (−)-strand sequencing (top strand template in FIG. 1) of deletions derived from pUC19C7 or pUC19H1, the 20mer 5'-GCTGCAAGGCGATTAAGTTG-3, was used; for (+)-strand sequencing (bottom strand template in FIG. 1) of deletions derived from pGEM-7Z14, the 20mers 5'-AGCTCTCCGGATCCAACCTT-3, or 5'-ATTTCACACAGGAAACAGCT-3' were used. Most reactions were run using 7-deaza-dGTP in place of dGTP to minimize compression artifacts during electrophoresis. Reactions were run with $^{35}$S-dATP (New England Nuclear, 5 μCi per labeling reaction), electrophoresed on 6% 40-cm acrylamide gels (BioRad) bonded to the outer plate of the electrophoresis assembly with 3-(trimethoxysilyl)propyl methacrylate (Aldrich), fixed 15 min. in 5% methanol/5% acetic acid, dried 30 min at 100° C., then autoradiographed overnight with Kodak XAR-5 film. Autoradiograms were read manually. Either Genepro (Riverside Scientific Enterprises, Seattle) or Pustell (International Biotechnology, Inc., New Haven) software was used for sequence analysis.

Radiochemical Dialkylglycine Decarboxylase Assay. Dialkylglycine decarboxylase activity was measured under zero-order conditions essentially as described (Dinwoodie and Boeker, 1979). Assay reactions contained 500 μL of protein solution (100 mM MOPS$^1$, (MOPS=3-(N-morphalino)propanesulfonic acid), 25 mM KCl, 0.05 mM PLP, (PLP=pyridoxal 5'-phosphate), pH 7.00 or 30 mM Tris, 40 mM KCl, 0.05 mM PLP pH 7.90) plus 0.045 mL of substrate solution (245 mM 2-methylalanine, 62 mM sodium pyruvate, containing 0.25 μCi [1-$^{14}$C]2-methylalanine). Assays were carried out in stoppered 12×220 mm test tubes containing a folded 10×25 mm piece of filter paper soaked with 24 μL of 2:1 ethanolamine/2-ethoxyethanol. After incubation at room temperature (25° C.) for one or two hours, the reaction was quenched with 200 μL of 50% trichloroacetic acid, $^{14}CO_2$ was collected for one hour, and the filter paper was counted in 10 mL of Beckman Ready Safe cocktail. One unit is defined as the amount of activity required to produce 1 nanomole of $CO_2$ per min. at 25° C.

Dialkylglycine Decarboxylase Purification. In a typical preparation four 400-mL cultures of *E. coli* JM109[pGEM-7Z14/8b] (LB containing 100 μg/mL carbenicillin) were grown with shaking at 37° C. until $A_{100}=4$. IPTG (final concentration =20 μg/mL) was added at $A_{600}=0.9$. The cells were cooled on ice, collected by centrifugation, resuspended in 40 mL buffer (30 mM Tris, 40 mM KCl, 500 mM ammonium sulfate, and 0.02 mM PLP), sonicated 3×1 min at 0° C., treated with 2 mg phenylmethylsulfonyl fluoride, and centrifuged for 20 min. at 14,000×g. The clarified extract was passed over at 1.5×5.1 cm column of butyl TSK (Toya Soda) (Shin et al., 1984) equilibrated with the same buffer. The column was washed with 50 mL of the same buffer then eluted with a 200-mL linear gradient to 30 mM Tris, 40 mM KCl, 0.02 mM PLP, pH 7.90. The active fractions (50–100 mL) were concentrated by ammonium sulfate precipitation, desalted on a small BioGel P-6 column (30 mM Tris, 40 mM KCl pH 7.90), and chromatographed in portions on a 8.0×75 mm DEAE 5-PW column eluted with a linear 40 to 500 mM KCl gradient (1 mL/min, 35 min.). The FPLC (fast protein liquid chromatography) active fractions (22–23 mL) were combined, concentrated with an Amicon centricon-30, and finally chromatographed on a Waters 300SW size exclusion column (10×300 mm, 0.8 mL/min.). The fraction under the major peak eluting at 8.9 min. was concentrated as above.

4'-$^3$H] Pyridoxal 5'-Phosphate. The labeled cofactor was prepared as described (Tamura and Rakov, 1986; Koga and Cross, 1982; Raibaud and Goldberg, 1974) by reduction of 25 mg PLP with [³H]NaBH₄ (25 mCi, 1400 mCi/mmol, in 0.30 mL 0.5M NaHCO₃ at 0° C.), oxidation with fresh MnO₂, and chromatography on a 1.5×28 cm Dowex-50 column (acetate form) to give material with a specific radioactivity of 260 mCi/mmol.

Active Site Labeling. Apodecarboxylase was made by incubating 1 mg of purified dialkylglycine decarboxylase with 2-methylalanine (40 mM plus 50 mM potassium phosphate pH 7.90, 50 mM KCl, and 0.020 mM PLP in a total volume 2.0 mL). After 5 h, the UV spectrum had changed from one of the characteristic of PLP ($\lambda_{max}$410,275 nm) to one characteristic of pyridoxamine 5'-phosphate ($\lambda_{max}$320 nm). The reaction was desalted on a 1×16 cm BioGel P6 column (50 mM potassium phosphate plus 50 mM KCl pH 7.90), reduced to 0.50 mL with a Centricon-30, and was treated with 0.20 mL ³H]PLP (1.5 mM). A 3-mg portion of NaBH₄ was added and after 1 h the reaction was desalted on a BioGel P6 column (1×16 cm, 50 mM Tris pH 7.8). Finally, the protein-containing fractions were concentrated to 0.70 mL using a Centricon-30.

Tryptic Peptide Mapping. The tritium-labeled and reduced decarboxylase (1 mg in 0.70 mL) was heated to 100° C. for 4 min, then 10 µl of trypsin (Sigma Type XI, DPCC-treated, 4 mg/mL in 50 mM Tris pH 7.5) was added and the reaction was shaken at 37° C. for 3 h; another 10 µl portion was added and the incubation was continued for 2 h. The cooled reaction was filtered through a 0.5-micron filter, then was injected (1 mL injection loop) onto a Vydac C-4 HPLC column (4.5×250 mm equilibrated with 0.12% aqueous trifluoroacetic acid and then eluted at 1 mL/min with a 120 min 0 to 40% acetonitrile, 0.12% trifluoroacetic acid gradient. Absorbance peaks were collected by hand and 50 µL aliquots of each were counted in 5 mL Beckman Ready Safe cocktail. The fraction containing the most radioactivity was rechromatographed under the same conditions and the radioactive fraction (which eluted at the same position) was lyophilized.

Protein Sequencing. A 10 µg sample of purified decarboxylase was desalted on a small BioGel P-6 column equilibrated with 1 mM ammonium acetate, then was lyophilized overnight. The protein was sequenced at the Bringham Women's Hospital of Harvard Medical School, Boston, Mass. The sample was dissolved in 100 µL of deionized water and was bound to a sample disk of an Applied Biosystems Inc. 470A automated protein sequencer. Twenty cycles were carried out with on-line PTH analyses. The labeled peptide was sequenced in the same manner in the Oncology Research Center Protein Sequencing Laboratory of the Bowman Gray School of Medicine in Winston-Salem, N.C. Sixty percent of each sequencer fraction was counted by liquid scintillation.

NMR Spectroscopy. ¹H-NMR spectra were obtained on a Varian EM-360 spectrometer. ¹³C-NMR were obtained on a JEOL FX90Q spectrometer.

Racemic Dialkylglycines. Racemic isovaline and 2-methylnorvaline were prepared by Strecker synthesis (Greenstein and Winitz, 1961) from butanone or 2-pentanone, respectively, and were purified by cation exchange chromatography on Dowex-50 followed by recrystallization from water-acetone, R,S-2-Methylnorvaline: sublimes 265°-270° C.; ¹H-NMR (D₂O):0.8δ (t,3H), 1.4 (s,3H), 0.9-1.9 (m,4H); ¹³CNMR (D₂O): 60δ(q), 64(t), 70(q), 87(t), 109(s), 224(s).

All other amino acids were obtained from Sigma Chem. Co.

Racemic N-Chloroacetyl Amides. These were prepared by reaction of the racemic amino acid with chloroacetyl chloride (1.5 equivalents) in a stirred aqueous solution at 0° C. maintained at pH>10 by addition of 2M sodium hydroxide. Amide was recovered by filtration of the acidified reaction mixture and was recrystallized from water. N-Chloroacetyl-R,S-isovaline: mp 161°-162° C.; ¹H-NMR (d₆-DMSO):0.78δ (t,3H), 1.35 (s,3H), 1.80 (q,2H), 4.1 (s,2H), 8.1 (s,1H). N-Chloroacetyl-R,S-2-methylnorvaline: mp 166°-166.5° C.; ¹H-NMR (d₆-DMSO) 1.0δ (t,3H), 1.5 (s,3H), 1.2-2.2 (m,4H), 4.3 (s,2H), 9.4 (s,1H).

S- and R-Dialkylglycines. The amino acid stereoisomers were prepared by partial enzymatic hydrolysis (Baker et al., 1952; Bosch et al., 1982) of the racemic N-chloroacetyl derivatives. Hydrolysis was carried out on the ammonium salt of each amide (0.2M, pH 7.5, 37° C.) by 3 mg/mL hog kidney aminoacylase (Sigma grade I). The reaction progress was followed by ¹H-NMR spectroscopy. Integration of the chloroacetyl methylene singlets (amide; 4.3δ; chloroacetate: 4.2δ) showed that the hydrolyses proceeded to 50% completion after 6–12 h and then stopped. The S isomer released by enzymatic hydrolysis was isolated by precipitating protein with 5% v/v trifluoroacetic acid and centrifuging, evaporating the supernatant, and eluting from Dowex-50 (H form). The R isomer was produced by hydrolyzing amide unretained by the initial Dowex-50 chromatography (2M HCl, 5 h at reflux), neutralizing with base, and again eluting from Dowex-50 (H form).

Induction of Dialkylglycine Decarboxylase. A 15-mL portion of YT (50 µg/mL ampicillin) in a 100-mL conical flask was inoculated with one of several strains of JM109 transformed with either pGEM-7Z14 or a partially deleted derivative. In some experiments 20 mM 2-methylalanine or other amino acid or 1 mg/mL IPTG was added to the growth medium. After growing overnight at 37° C. with shaking, the culture was cooled on ice, and the bacteria were harvested by centrifugation, resuspended in 2 mL MOPS buffer, sonicated 30 s, centrifuged (10,000×g), and 0.50 mL of the supernatant was assayed for decarboxylase activity. Protein concentrations were determined by dye binding (Read and Northcote, 1981).

Time Course of Dialkylglycine Decarboxylase Induction. An 800-mL portion of M9 containing 12 µg/mL tetracylcine in a 6-L conical flask was inoculated with DH5α/pKBD6. The flask was shaken at 37° C. and the absorbance at 600 nm was measured periodically. At various times during cell growth aliquots containing 60. AU's (absorbance units) of cells were removed, stored on ice, concentrated by centrifugation, and resuspended in 1.0 mL MOPS buffer. Aliquots of 0.50 mL were assayed for dialkylglycine activity. After the first two samples were taken, an amino acid (2-methylalanine, R,S-isovaline, D-alanine, or L-alanine) was added to a final concentration of 8.0 mM and sampling was continued.

RESULTS

| Purification of Recombinant 2,2-Dialkylglycine Decarboxylase | | | | |
| --- | --- | --- | --- | --- |
| | Protein (mg) | Total U$^a$ | U$^a$/mg protein | Yield (%) |
| Cell Sonicate | 260. | 1710 | 8.6 | 100 |
| Butyl-TSK | 4.8 | 710 | 148. | 42 |
| DEAE-5PW | 0.201 | 669 | 3400 | 39 |

| Purification of Recombinant 2,2-Dialkylglycine Decarboxylase | | | | |
|---|---|---|---|---|
| | Protein (mg) | Total U[a] | U[a]/mg protein | Yield (%) |
| 300SW | 0.126 | 306 | 2430 | 18 |

[a]1 unit = 1 nmol $CO_2$ per minute at pH 7.90, 25° C.

Following are the citations of publications cited in the foregoing text.

REFERENCES

Aaslestad, H. G., and Larson, A. D. (1964) J. Bacteriol. 91, 1296–1303

Aaslestad, H. G., Bouis, Jr., P. J., Phillips, A. T., and Larson, A. D. (1968) in Pyridoxal Catalysis: Enzymes and Model Systems (Snell, E. E., Braunstein, A. E., Severin, E. S., and Torchinsky, Yu M., eds) pp. 479–490. Wiley Interscience, New York Bailey, G. B., and Dempsey, W. B. (1967) Biochemistry 6, 1526–1533

Bailey, G. B., Chotamangsa, O., and Vuttivej, K. (1970) Biochemistry 9, 3243–3248

Baker, C. G., Fu, S.-C. J., Birnbaum, S. M., Sober, H. A., and Greenstein, J. P. (1952) J. Am. Chem. Soc. 74, 4701–4702

Baurick, K. B. (1987) M. S. Thesis, University of Alaska, Fairbanks

Bibb, M. J., Findlay, P. R., and Johnson, M. W. (1984) Gene (Amst.) 30, 157–166

Borisov, V. V., Borisova, S. N., Sofenov, N. L., and Wainshtein, B. K. (1980) Nature 284, 189–191

Bosch, R., Bruckner, G., Jung, G., and Winter, W. (1982) Tetrahedron 38, 3579–3583

Bruckner, H., and Pryzbylski, M. (1984) J. Chromatog 296, 263–275

Bruckner, H., Nicholson, G. J., Jung, G., Kruse, K., and Konig, W. A. (1980) Chromatographia 13, 209–214

Bulmer, M. (1988) J. Theoret. Biol. 133, 67–71

Cornish-Bowden, A. (1979) J. Theoret. Biol. 76, 369–386

Degols, G. (1987) Eur. J. Biochem. 169, 193–200

Dinwoodie, R. C., and Boeker, E. A. (1979) Anal. Biochem. 96, 24–38

Doonan, S., Doonan, H. J., Hanford, R., Bernon, C. A., Walker, J. M., Airoldi, L., Bossa, F., Barra, D., Carloni, M., Fasella, P., and Riva, F. (1975) Biochem. J. 149, 497–506

Fischer, E. H., Kent, A. B., Snyder, E. R., and Krebs, E. G. (1958) J. Am. Chem. Soc. 80, 2906–2907

Ford, G. C., Eichele, G., and Jansonius, J. N. (1980) Proc. Natl. Acad. Sci. U.S.A. 77, 2559–2563

Fotheringham, I. G., Dacey, S. A., Taylor, P. P., Smith, T. J., Hunter, M. G., Finlay, M. E., Primrose, S. B., Parker, D. M., and Edwards, R. M. (1986) Biochem. J. 234, 593–604

Golub, E. I. (1988) Nucleic Acids Res. 16, 1641

Graf-Houser, U., Wilson, K. J., and Christen, P. (1983) J. Biol. Chem. 258, 8813–8826

Greenstein, J. P., and Winitz, M. (1961) Chemistry of the Amino Acids, Vol. 3, p. 2565, Wiley Interscience, New York Hayashi, H., Tanase, S., and Snell, E. E. (1986) J. Biol. Chem. 261, 11003–11009

Henikoff, S. (1984) Gene (Amst.) 28, 351–359

Henikoff, S., and Wallace, J. C. (1988) Nucleic Acids Res. 16, 6191–6204

Holmes, D. S., and Quigley, M. (1981) Anal. Biochem. 114, 193–197

Honma, M., Ikeda, M., and Shimomura, T. (1972) Agric. Biol. Chem. Tokyo 36, 1661–1666

Inoue, K., Kuramitsu, S., Aki, K., Watanabe, Y., Takagi, T., Nishigai, A., and Kagamiyama, H. (1988) J. Biochem. (Tokyo) 104, 777–784

Jansonius, J. N., Eichele, G., Ford, G. C., Picot, D., Thaller, C., and Vincent, M. G. (1985) in Transaminases (Christen, P., and Metzler, D. E., eds) pp. 109–137, Wiley Interscience, New York Kagamiyma, H., Sakakibara, R., Tanase, S., Morino, Y., and Wada, H. (1980) J. Biol. Chem. 255, 6153–6159

Keller, J. W., and O'Leary, M. H. (1979) Biochem. Biophys. Res. Commun. 90, 1104–1110

Koga, P. G., and Cross, R. L. (1982) Biochim. Biophys. Acta 679, 269–278

Kraft, R., Tardiff, J., Krauter, K. S., and Leinwand, L. A. (1988) Biotechniques 6, 544–546

Kvenvolden, K. A., Lawless, J. G., and Ponnamperuma, C. (1971) Proc.Natl. Acad. Sci. U.S.A. 68, 486–490

Lamartiniere, C. A., Itoh, H., and Dempsey, W. B. (1971) Biochemistry 10, 4783–4788

Maniatis, T., Fritsch, E. F., and Sambrook, J. (1982) Molecular Cloning: A Laboratory Manual, Cold Spring Harbor Laboratory, Cold Spring Harbor, N.Y.

Min, T. M., Kim, M. H., and Lee, D. S. (1988) Nucleic Acids Res. 16, 5075–5088

Mitchell, G. A., Looney, J. E., Brody, L. C., Steel, G., Suchanek, M., Engelhardt, J. F., Willard, H. F., and Valle, D. (1988) J. Biol. Chem. 263, 14288–14295

Mueckler, M. M., and Pitot, H. C. (1985) J. Biol. Chem. 260, 12993–12997

Needleman, S. B., and Wunsch, C. D. (1970) J. Mol. Biol. 48, 443–453

Oda, T., Miyajima, H., Suzuki, Y., and Ichiyama, A. (1987) Eur. J. Biochem. 168, 537–542

Platt, T. (1986) Annu. Rev. Biochem. 55, 339–372

Raibaud, O., and Goldberg, M. E. (1974) FEBS Lett. 40, 41–44

Reed, S. M., and Northcote, P. H. (1981) Anal. Biochem. 116, 53–64

Sanger, F., Nicklen, S., and Coulson, A. R. (1977) Proc. Natl. Acad. Sci. U.S.A. 74, 5463–5467

Sato, S., Honma, M., and Shimomura, T. 1978) Agric. Biol. Chem. Tokyo 42, 2341–2346

Schmitt, H., and Jung, G. (1985) Liebig's Ann. Chem. 1985, 321–344

Shin, M., Sakihama, N., Oshino, R., and Sasaki, H. (1984) Anal. Biochem. 138, 259–261

Simmaco, M., John, R. A., Barra, D., and Bossa, F. (1986) FEBS Lett. 199, 39–42

Sober, H. A. (1968) Handbook of Biochemistry, p. H-31, Chemical Rubber Co., Cleveland Stormo, G. D., Schneider, T. D., and Gold, L. M. (1982) Nucleic Acids Res. 10, 2971–2996

Sukhareva, B. (1986) Vitamin B-6. Chemical, Biochemical, and Medical Aspects (Dolphin, D., Poulson, R., and Avramovic, O., eds) Part B, pp. 337–343, Wiley Interscience, New York Tahara, S., Honma, M., and Shimomura, T. (1969) Mem. Fac. Agric. Hokkaido Univ. 7, 12–18

Tamura, J. K., and Rakov, R. D. (1986) J. Biol. Chem. 261, 4126–4133

Tanase, S., Kojima, H., and Morino, Y. (1979) Biochemistry 18, 3002–3007

Vaaler, G. L., and Snell, E. E. (1989) Biochemistry 28, 7306–7313 van del Zel, A., Lam, H.-M., and Winkler, M. W. (1989) Nucleic Acids Res. 17, 8379

Wilbur, W. J., and Lipman, D. J. (1983) Proc. Natl. Acad. Sci. U.S.A. 80, 726–730

Yanisch-Perron, C., Viera, J., and Measing, J. (1985) Gene (Amst.) 33, 103–119

Zhao, M., and Bada, J. L. (1989) Nature 339, 463–465

What is claimed is:

1. A process for obtaining *Pseudomonas cepacia* 2,2-dialkylglycine decarboxylase, which comprises:
   (A) providing a biomass comprised of *E. coli* cells transformed or transfected with the recombinant expression vector pKBD6; and
   (B) culturing said *E. coli* cells in the presence of a transcriptional inducing agent selected from the group consisting of L-2-aminobutanoic acid and 1-aminocyclopentanecarboxylic acid;
   wherein said agent is employed in said biomass in an amount sufficient to induce transcription of said *Pseudomonas cepacia* 2,2-dialkylglycine decarboxylase gene.

2. A process for obtaining *Pseudomonas cepacia* 2,2-dialkylglycine decarboxylase, which comprises:
   (A) providing a biomass comprised of *E. coli* cells transformed or transfected with the recombinant expression vector pUC19C7; and
   (B) culturing said *E. coli* cells in the presence of a transcriptional inducing agent selected from the group consisting of L-2-aminobutanoic acid and 1-aminocyclopentanecarboxylic acid;
   wherein said agent is employed in said biomass in an amount sufficient to induce transcription of said *Pseudomonas cepacia* 2,2-dialkylglycine decarboxylase gene.

3. A process for obtaining *Pseudomonas cepacia* 2,2-dialkylglycine decarboxylase, which comprises:
   (A) providing a biomass comprised of *E. coli* cells transformed or transfected with the recombinant expression vector pGEM-7Z14; and
   (B) culturing said *E. coli* cells in the presence of a transcriptional inducing agent selected from the group consisting of L-2-aminobutanoic acid and 1-aminocyclopentanecarboxylic acid;
   wherein said agent is employed in said biomass in an amount sufficient to induce transcription of said *Pseudomonas cepacia* 2,2-dialkylglycine decarboxylase gene.

* * * * *

UNITED STATES PATENT AND TRADEMARK OFFICE
CERTIFICATE OF CORRECTION

PATENT NO. : 5,210,025
DATED : May 11, 1993
INVENTOR(S) : John W. Keller

It is certified that error appears in the above-indentified patent and that said Letters Patent is hereby corrected as shown below:

Column 1, line 1, before the text, insert the following paragraph:

This invention was made with government support under Grant No. DMB-8704139 of the National Science Foundation. The government has certain rights in the invention.

Signed and Sealed this

Seventeenth Day of December, 1996

Attest:

BRUCE LEHMAN

*Attesting Officer*  *Commissioner of Patents and Trademarks*